United States Patent [19]

Silberstein et al.

[11] Patent Number: 5,322,838
[45] Date of Patent: Jun. 21, 1994

[54] USE OF INHIB (THE C3 β-CHAIN) IN THE DETECTION AND INHIBITION OF INFLAMMATION

[75] Inventors: David S. Silberstein, Medfield; Marjorie Minkoff, Boston, both of Mass.

[73] Assignee: Brigham & Women's Hospital, Boston, Mass.

[21] Appl. No.: 779,172

[22] Filed: Oct. 16, 1991

Related U.S. Application Data

[63] Continuation-in-part of Ser. No. 271,863, Nov. 16, 1988, abandoned.

[51] Int. Cl.$^5$ ............................................. A61K 37/00
[52] U.S. Cl. ......................................... 514/21; 514/2; 514/12; 514/885; 514/903; 514/825; 530/380; 530/388.23; 530/388.24; 530/389.2; 436/506
[58] Field of Search ............... 514/2, 12, 21, 885, 514/903, 825; 530/380, 388.23, 388.24, 389.2; 436/506

[56] References Cited

U.S. PATENT DOCUMENTS

| | | | |
|---|---|---|---|
| 4,376,110 | 3/1983 | David et al. | 436/513 |
| 4,645,748 | 2/1987 | Hurwitz et al. | 436/509 |
| 4,840,793 | 6/1989 | Todd, III et al. | 424/85.8 |

OTHER PUBLICATIONS

Kuivanen, et al. Biochem. Biophys. Research Comm. 158(3), 898–905 (1989).
Milstein, et al. Nature 256, 495–7 (1975).
Muchmore, et al., *Science*, 229:479–81 (1985).
Seckinger, et al., *J. Exp. Med.*, 167:1511–16 (1988).
Lin et al., *Immunology*, 63:663–68 (1988).
Silberstein, et al., *J. Immunol.*, 143(3):979–83 (1989).
Silberstein, et al., *J. Immunol.*, 142(6):2162–67 (1989).
Lamas, et al., *J. Immunol.*, 140(5):1500–05 (1988).

*Primary Examiner*—Michael G. Wityshyn
*Assistant Examiner*—C. Sayala
*Attorney, Agent, or Firm*—Sterne, Kessler, Goldstein & Fox

[57] ABSTRACT

The present invention relates to the use of INHIB in the detection and inhibition of inflammation. INHIB is structurally identical to the C3 β-chain.

8 Claims, 20 Drawing Sheets

USE OF INHIB (THE C3 β-CHAIN) IN THE DETECTION AND INHIBITION OF INFLAMMATION

This invention was made in part with Government support. The Government has certain rights in this invention.

This is a continuation-in-part of U.S. Ser. No. 07/271,863, filed Nov. 16, 1988, now abandoned.

BACKGROUND OF THE INVENTION

1. Field of the Invention

The present invention relates to the identification and substantial purification of a factor (INHIB) that inhibits the immunologic activity of cytokine-stimulated leukocytes. This factor is shown to be the free β chain of complement C3.

The invention additionally relates to processes for preparing the INHIB molecule, methods of purifying the molecule, screening assays for the molecule, compositions containing INHIB, and uses for the molecule.

2. Description of the Related Art

Levels of circulating eosinophils and other types of leukocytes are elevated in conditions such as allergy, asthma, parasitic diseases, autoimmune disorders such as connective tissue disease, in certain types of cancer, and in patients undergoing therapy with interleukin-2 (IL-2) or granulocyte-macrophage colony-stimulating factor. Leukocytes, in particular eosinophils, persist in the circulation with a half-life of several hours to two days and then either enter the marginated (blood vessel wall) pool or infiltrate tissues. At the site of inflammation in tissue, eosinophils and neutrophils, for example, secrete toxic substances that may kill infectious organisms but also may damage host (patient) tissues. For example, in the condition known as idiopathic hypereosinophilic syndrome, eosinophil cytotoxins cause ultrastructural damage and progressive fibrosis in the major organ systems, and ultimately lead to death due to cardiac or respiratory arrest, or liver failure.

Current treatment of leukocyte-mediated inflammatory disease consists of administering a variety of anti-inflammatory, antiproliferative, or cytotoxic drugs including prednisone, vincristine, and hydroxyurea. The efficacy of these drugs varies, depending on the disease state but there is no good treatment for idiopathic hypereosinophilic syndrome, for example. All of the drugs currently used therapeutically can have severe side effects on the subject. Similarly, there is an absence of effective drug treatments for many types of inflammatory diseases (such as rheumatoid arthritis) which involve inflammatory cells other than eosinophils.

Several research groups have identified substances from biological sources that have inhibitory activity in vitro in assays that may correlate with processes in inflammation (processes that do not involve eosinophil function). These purified substances presumably may have some efficacy in the treatment of inflammatory disease; for example, uromodulin (Muchmore et al., Science 229:479 (1985), J. Biol. Chem. 259:13404 (1984), and 263:5418 (1988)), and undefined activities that protect L929 tumor cells from the toxic effects of tumor necrosis factor (TNF) (Seckinger et al., J. Exp. Med. 167:1511 (1988) and Lin et al., Immunology 63:663 (1988)). Uromodulin, for example, binds with high affinity to interleukin-1 (IL-1) and to TNF, suggesting that its activity is specific for cellular events mediated by these two factors.

It is also possible that the processing of biological fluids may produce substances with apparent anti-inflammatory activities (Justement et. al., J. Nat. Cancer Inst. 73:469). This group showed that chromatography of low density and very low density lipoproteins can oxidize the lipid moieties of these molecules, producing a molecule that inhibits monocyte cytotoxic function.

Abundant evidence demonstrates that eosinophil cytotoxic function can be enhanced by a number of immunological mediators, but there was no previous evidence of an immunological mechanism to suppress this function.

Current treatment modalities for inflammatory disease are very unsatisfactory. Any means capable of attenuating or inhibiting cellular mechanisms of inflammation would, therefore, be highly desirable for subjects suffering from certain inflammatory disease processes.

SUMMARY OF THE INVENTION

This invention relates to a factor which inhibits the immunological activity of cytokine-stimulated leukocytes, in particular eosinophils and neutrophils. This factor, called INHIB, which suppresses proinflammatory functions, may be found in sera and various other biological tissues and fluids. This factor consists of a single polypeptide species having the amino acid sequence of SEQ ID NO. 3 and has a molecular weight (MW) of approximately 70 kilodaltons. Its activity is destroyed by either heating at 80° C. or by treatment with trypsin, demonstrating that it is a polypeptide.

A computer comparison of a structural component of INHIB with the known structure of the free β chain of complement C3 indicates that there is substantial similarity between the two proteins. Having now sequenced fully INHIB, it is known that INHIB and the free β chain of complement C3 are, in fact, the same molecule. Further analysis shows that this free β chain also suppresses proinflammatory functions.

During the course of molecular sizing HPLC, it was discovered that the potency of INHIB increased. When serum from a subject with allergic dermatitis was used as a source of INHIB, the HPLC increased the potency of INHIB by a factor of 50 to 2000 in multiple experiments. INHIB was also derived by HPLC fractionation of control serum from each of many other subjects, demonstrating that INHIB is a component of normal biological fluid and tissue that can be activated by purification and, presumably, by certain physiological events in vivo.

The present invention relates to INHIB as well as to its functional derivatives. The invention additionally pertains to processes for preparing and purifying INHIB, screening assays for INHIB, diagnostic and therapeutic uses of INHIB, and compositions containing INHIB or its functional derivatives.

In particular, the invention includes INHIB or its functional derivatives, which are substantially free of natural contaminants.

The purification of INHIB was achieved by a sequence of protein fractionation methodologies. Following each separation step, the fractions were screened for the ability to inhibit eosinophil killing of targets in vitro. The fractions containing the major inhibitory activity were forwarded to the next separation methodology.

The invention includes a method for recovering INHIB in substantially pure form which includes, but is not limited to, the following steps:

(a) isolating INHIB from a sample;
(b) ammonium sulfate precipitation of the INHIB-containing fraction;
(c) controlled-pore glass bead chromatography of the INHIB-containing fraction;
(d) hydrophobic interaction chromatography of the INHIB-containing fraction;
(e) anion exchange chromatography of the INHIB-containing fraction;
(f) reverse-phase HPLC chromatography of INHIB; and
(g) recovering the filtrate obtained in step (f) in substantially pure form.

Purified and partially purified INHIB suppressed the killing of targets by eosinophils stimulated with granulocyte-macrophage colony stimulating factor as well as with TNF. This demonstrates that the activity of INHIB is not cytokine-specific.

Purified and partially-purified INHIB suppressed the adherence of tumor necrosis factor (TNF)-stimulated neutrophils to plastic surfaces. This demonstrates that the inhibitory activity of INHIB is not restricted to eosinophils but rather regulates a variety of inflammatory cell types.

The purification of INHIB also permits the generation of INHIB-related oligonucleotide and antibody probes that can be used to screen gene libraries for the molecular cloning of the INHIB gene. For logistical reasons, culture medium containing biosynthetic (recombinant) INHIB would be a superior source material compared to natural biological tissues or fluids for the purification of INHIB. The purification strategy presented here may be used to purify recombinant INHIB.

The invention includes the INHIB obtained by the above methods.

The invention further pertains to INHIB and its derivatives which are detectably labeled.

The invention is further directed to a method of diagnosing the presence and location of inflammation in a mammalian subject suspected of having an inflammation which comprises: (a) administering to said subject a composition containing a detectably labeled binding molecule (e.g., antibody) capable of binding and identifying INHIB; and (b) detecting said binding molecule.

The invention also pertains to a method of diagnosing the presence and location of an inflammation in a mammalian subject suspected of having an inflammation which comprises: (a) incubating a biological sample from said subject suspected of containing INHIB in the presence of a detectably labeled binding molecule (e.g., antibody) capable of identifying INHIB; and (b) detecting said binding molecule which is bound in said sample. Said biological samples may include various tissues or body fluids such as blood serum, for example.

The invention is also directed to a method of treating inflammation in a mammalian subject which comprises providing to said subject in need of such treatment an amount of an anti-inflammatory agent sufficient to suppress said inflammation; wherein said anti-inflammatory is selected from the group consisting of: INHIB, a fragment of INHIB, a chemical derivative of INHIB, a variant of INHIB, and an analogue of INHIB.

The invention also includes the above method for treating inflammation wherein said anti-inflammatory agent is administered in a suitable carrier.

The invention is also directed to a method for treating inflammation wherein the free $\beta$ chain of complement C3 is administered in a suitable carrier.

The invention also relates to a pharmaceutical composition for treating inflammation in a mammalian subject comprising administering an inflammation-reducing amount of an anti-inflammatory agent, wherein said agent is selected from the group consisting of: INHIB, a fragment of INHIB, a chemical derivative of INHIB, a variant of INHIB, and an analogue of INHIB.

The invention therefore includes novel methods for recovering and purifying the new INHIB molecule and its functional derivatives, uses for the molecule, including diagnosing and treating inflammation in a mammalian subject, and novel compositions containing INHIB or its functional derivatives.

An understanding of this process of the inhibition of immunologic activity of cytokine-stimulated leukocytes such as eosinophils and neutrophils, and of the natural anti-inflammatory INHIB molecule itself, will aid in the development of its therapeutic and/or diagnostic uses in such fields as organ transplantation, allergy and oncology. This invention will enable those in the medical field to more effectively diagnose and treat inflammatory disease processes, and to utilize a quantitative assay for INHIB in order to monitor the time-course and/or intensity of ongoing clinical episodes of inflammation. The invention will further enable researchers to investigate the mechanisms of leukocyte interactions and leukocyte function, particularly eosinophils and neutrophils, in inflammation.

BRIEF DESCRIPTION OF THE FIGURES

FIG. 1(A). Summary of 40 experiments, using eosinophil purified from 21 different donors (excluding NR).

FIG. 1(B). Summary of 12 experiments using eosinophils purified from NR, each done in parallel with at least from experiment in group A. Experiments U and W were done while NR was undergoing severe contact dermatitis reactions. Experiment Y was done while NR had extensive bruising as a result of an accidental fall.

FIG. 1(C). The responsiveness of NR eosinophils (solid circle) and normal eosinophils (open triangles) to TNF at the indicated doses. The levels of killing in the absence of TNF are shown for NR (dotted line) and normal (dashed line) eosinophils.

FIG. 8(A). 100 ul of NR serum was injected on a TSK 400 column, and 1 ml fractions were collected. The fractions were heat-inactivated (56° for 30 minutes) and added to TNF-stimulated eosinophils at a concentration of 20%. The cytotoxic function of the eosinophils was determined at 36 to 40 hours.

DESCRIPTION OF THE PREFERRED EMBODIMENTS

Figure 1B:
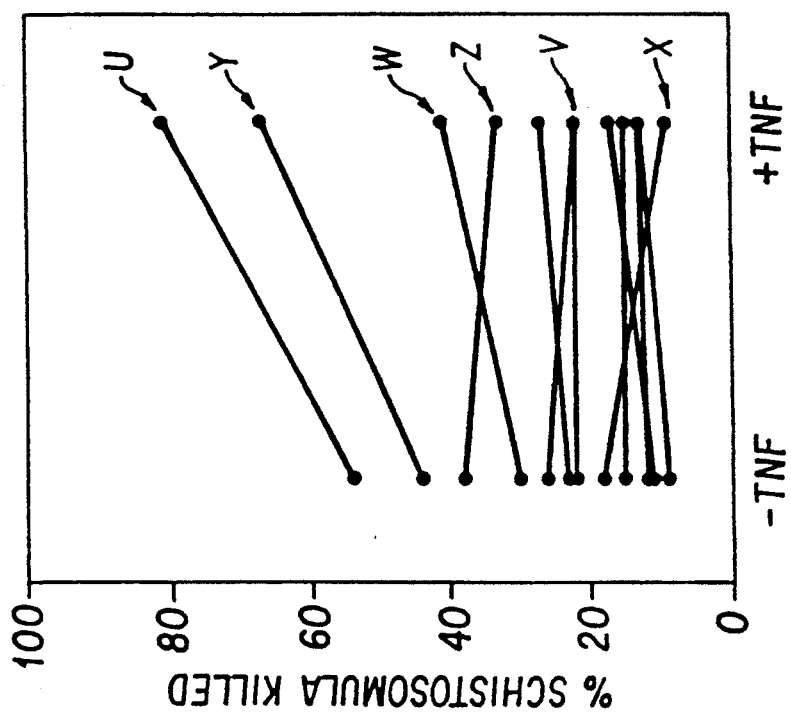
FIGS. 1(A)-1(C). The failure of eosinophils from a human subject (NR) to respond with enhanced cytotoxic function to TNF. Normal and NR eosinophils were purified and cultured in the presence of schistosomula targets, antibody, and either 100 U/ml or the indicated concentration of TNF. The killing of schistosomula targets was scored in duplicate or triplicate by microscopy at 36 to 40 hours.
Figure 1A:
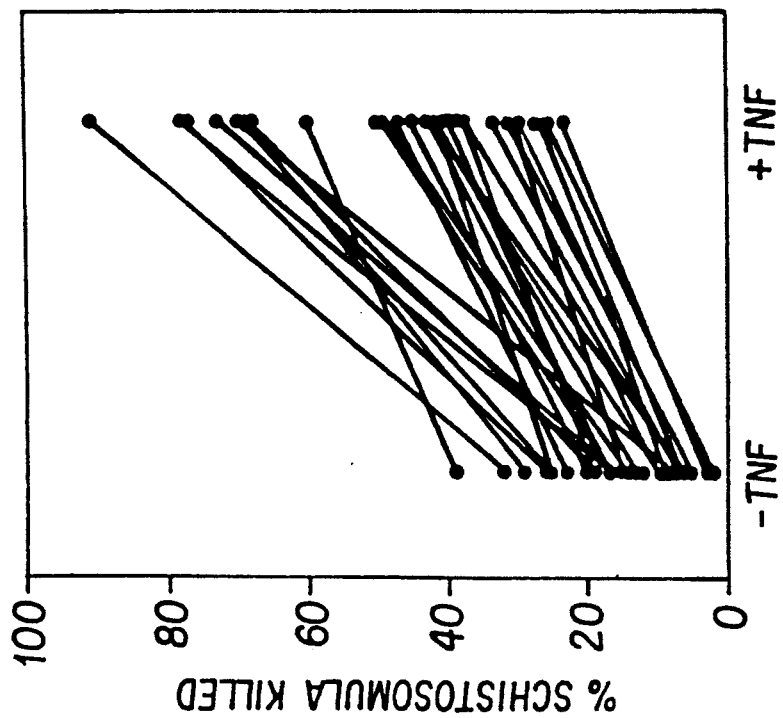
Figure 1C:
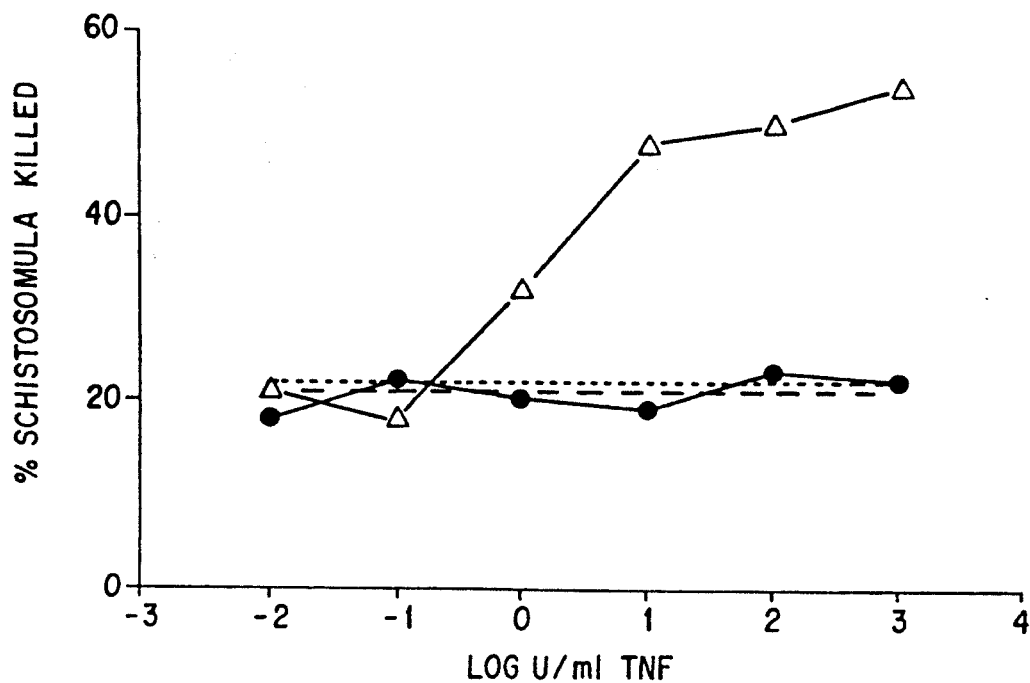
Figure 2:
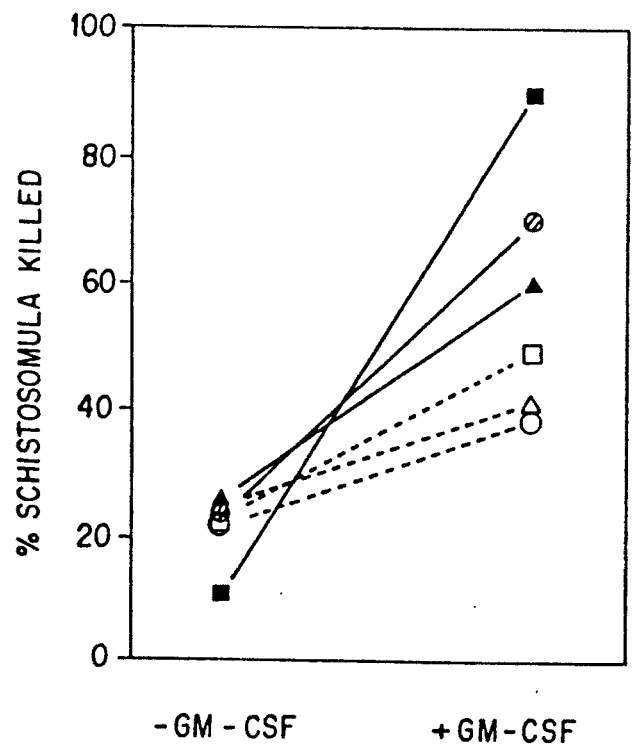
FIG. 2. Weak response of NR eosinophil to GM-CSF. In parallel with 3 experiments from FIGS. 1A and 1B, the effect of GM-CSF was tested on the cytotoxic function of NR eosinophils that were unresponsive TNF (open symbols). The responsiveness was compared to that of normal eosinophils (solid symbols of the same shape).
Figure 3A:
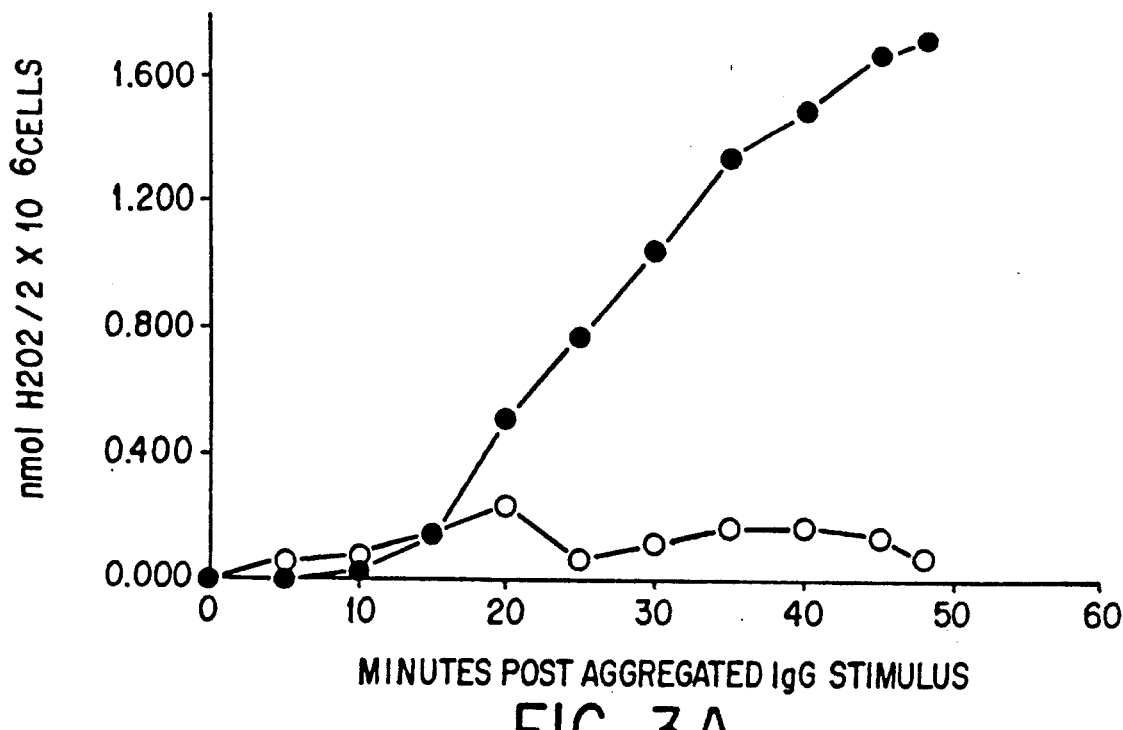
FIGS. 3A and 3B. The failure of NR neutrophils to respond with enhanced respiratory burst to TNF. Neutrophils from a normal subject FIG. 3A and NR FIG. 3B were isolated and incubated in physiological buffer at 37° for 10 minutes with (solid circles) or without (open circles) 100 U/ml of TNF. At time 0 the neutrophils were treated with 50 μg/ml of IgG aggregates and incubated further at 37° C. The release of H$_2$O$_2$ over time was monitored by the scopoletin method. TNF alone did not stimulate the release of H$_2$O$_2$ (not shown).
Figure 3B:
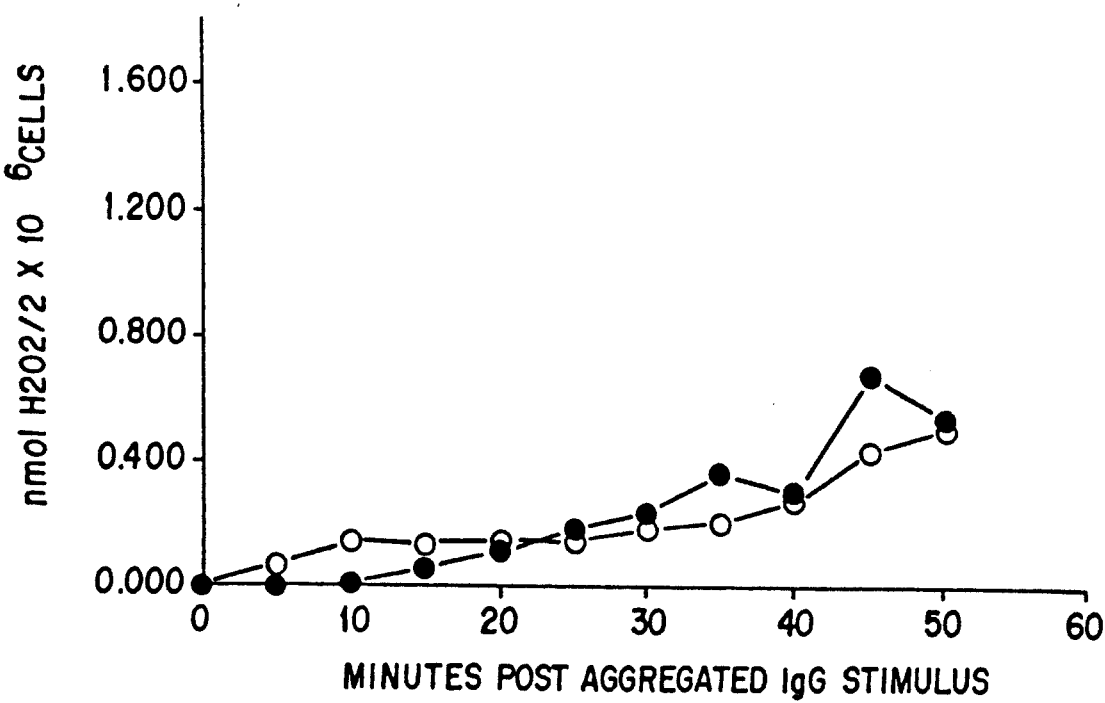
Figure 4:
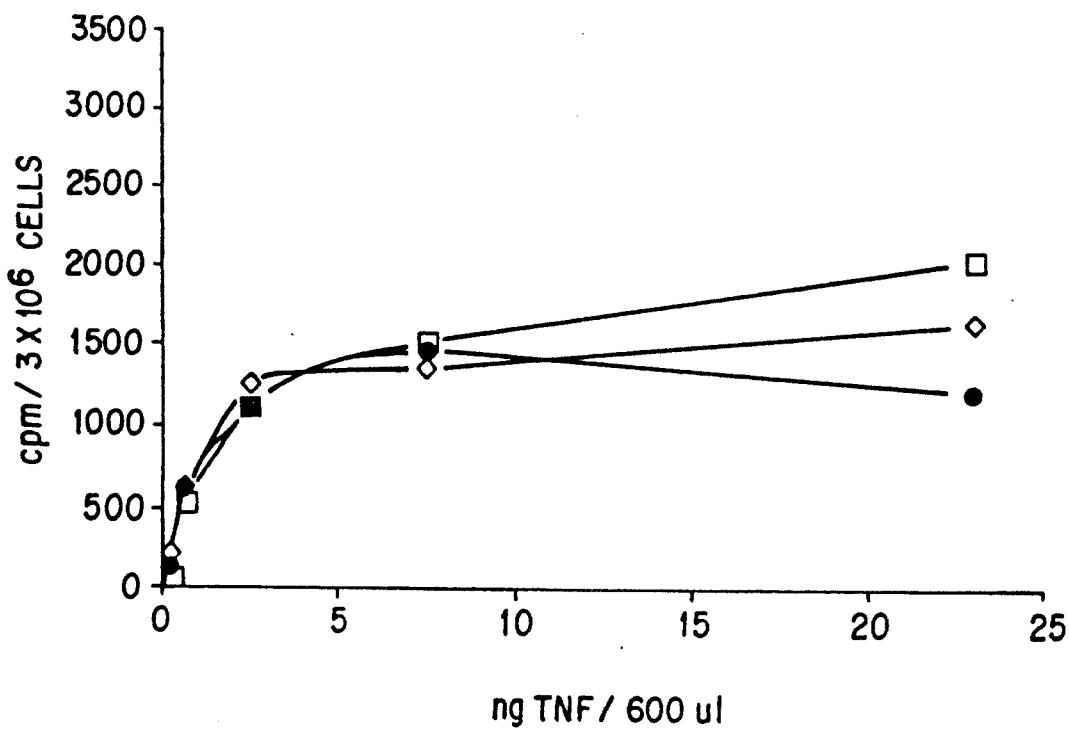
FIG. 4. Specific binding of $^{125}$I-TNF to NR neutrophils (solid circles) and to normal neutrophils from 2 different subjects (open symbols). 3×10$^6$ neutrophils were incubated overnight with either the indicate dose of labeled TNF (for total cpm bound) or that does plus a 1000-fold excess of unlabeled TNF (for non-specific cpm bound). Non-specific cpm bound was subtracted from total cpm bound to determine the specific cpm bound at each concentration. At doses of less than 15 ng TNF/600 ul, non-specific cpm bound were <26% of total cpm.
Figure 5:
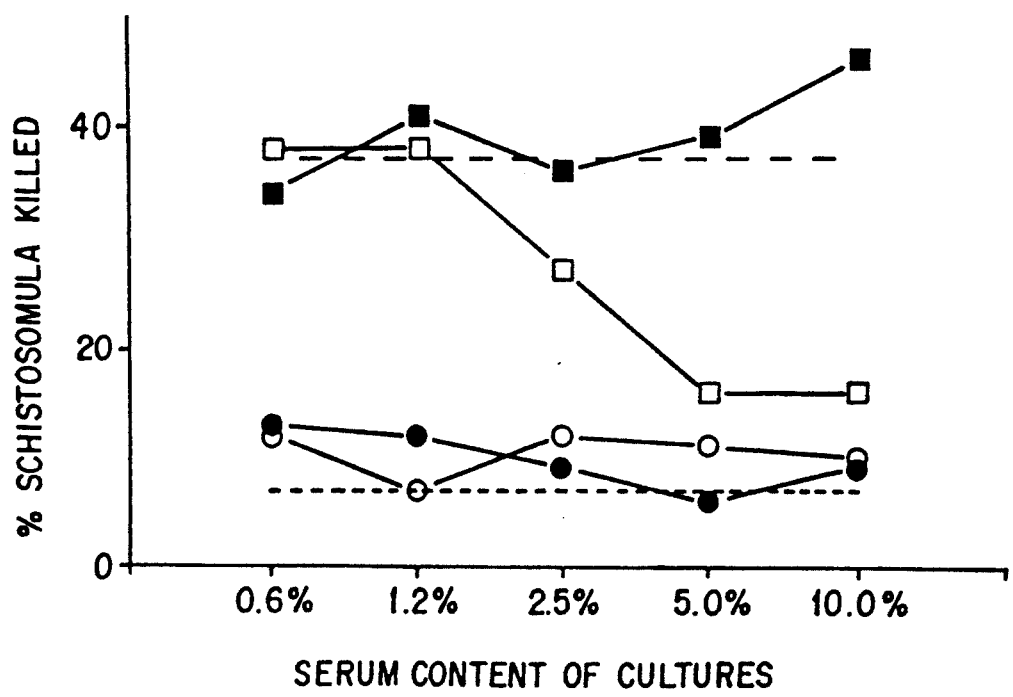
FIG. 5. The ability of NR serum to cross-inhibit heterologous eosinophils from responding to TNF. The cytotoxic function of eosinophils was assayed in the presence (squares) or absence (circles) of 100 U/ml of TNF. Control heterologous serum (solid) or NR serum (open) was added to the cultures at the indicated concentrations. The horizontal lines indicate the level of killing with no serum added in the presence (dashes) or absence (dots) of TNF.
Figure 6:
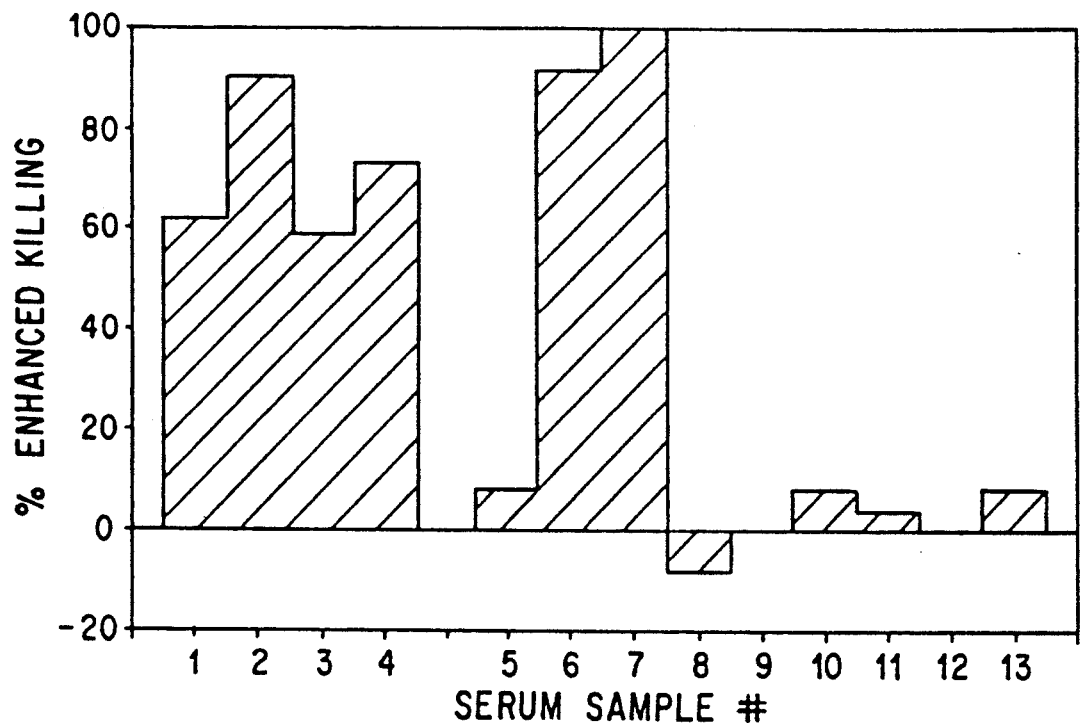
FIG. 6. Variation over time in the ability of NR serum to inhibit the cytotoxic function of TNF-stimulated eosinophils. The cytotoxic function in the presence (100%) or absence (0%) of 100 U/ml TNF was assayed. Heterologous (with respect to the eosinophils) sera were added to the cultures at a concentration of 10%. Samples 1-4 were taken from control donors.

One aspect of the present invention relates to the discovery of a natural inhibitor of cytokine-stimulated leukocyte immunological activity, referred to as INHIB. The invention is directed toward substantially pure INHIB and its "functional derivatives."

The term "leukocyte" refers to white blood cells, including neutrophils,

By the terms "activated," "activation," or "immunologic activity" is meant the stimulation of subject cells to behave in a certain biologically expected manner, i.e., for neutrophils to become adherent or eosinophils to become cytotoxic, for example.

The term "cytokine" refers to a compound capable of activating leukocytes, in particular, eosinophils and neutrophils. Cytokines are, in general, proteins or glycoproteins having a molecular weight of 10–100 kDa. Examples of cytokines are disclosed by Stephenson (In: *Animal Cell Biotechnology*, Vol. 2, Spier, R.E., et al., eds., Academic Press, pp. 41–45 (1985)). Although any compound capable of regulating INHIB inhibition of the immunological activities of leukocytes, such as cytotoxicity or adherence, may be employed in accordance with the present invention, it is preferable to employ a cytokine, and it is especially preferable to employ the cytokine TNF or granulocyte-macrophage colony-stimulating factor (GMCSF), or eosinophil cytotoxic enhancing factor (ECEF) and their recombinant forms. See, for example, Wang et al., Science 228:149 (1985) for the cloning and purification of recombinant TNF; and Wong et al., Science 228:810 (1985) for the cloning and purification of recombinant GMCSF. The regulation of human eosinophil function by cytokines is described in Silberstein et al., *Immunol. Today* 8:380–385 (1987).

The term "functional derivatives" is intended to include the "fragments," "variants," "analogues," or "chemical derivatives" of a molecule. A "fragment" of a molecule such as INHIB is meant to refer to any polypeptide subset of that molecule. A "variant" of a molecule such as INHIB is meant to refer to a naturally occurring molecule substantially similar to either the entire molecule, or a fragment thereof. An "analogue" of a molecule such as INHIB is meant to refer to a non-natural molecule substantially similar to either the entire molecule or a fragment thereof. A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

For example, TABLE THREE indicates that INHIB and the free $\beta$ chain of complement C3 are substantially similar to one another. That is, a comparison of the structure of the two proteins does not demonstrate that all amino acids are identical. Nevertheless, the Examples herein indicate that INHIB and the free $\beta$ chain of complement C3 are capable of inhibiting inflammation. This indicates that as long as INHIB retains the conformational structure of the functional free $\beta$ chain, INHIB will be capable of functioning as an anti-inflammatory agent. In fact, it is now known that INHIB and the free $\beta$ chain of C3 are the same molecule.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

One screening method for determining whether a given compound is an INHIB functional derivative comprises, for example, immunoassays employing RIA or ELISA methodologies, based on the production of specific neutralizing antibodies (monoclonal or polyclonal) to natural INHIB. Other suitable screening methods will be readily apparent to those of skill in the art.

The INHIB molecule disclosed herein is said to be "substantially free of natural contaminants" if preparations which contain it are substantially free of materials with which this product is normally and naturally found.

For purposes of the present invention, preferred methods of purification or separation of INHIB from a sample include, without being limiting, the following steps:

a) Fractionating the biological sample containing INHIB based on precipitating proteins at high ionic strength. Proteins differ in their solubility in concentrated salt solutions and hence can be separated from one another by precipitation at high ionic strength. The preferred salt is ammonium sulfate, although other salts are known and may be used.

b) Protein separation based on hydrogen bonding to separate the contaminating proteins from the sample containing INHIB using hydrophobic interaction chromatography. This step is preferably chromatography over controlled-pore glass beads such as those available from Sigma Chemical Co., St. Louis, Mo., when the biological sample is serum. Alternatively, for other samples, DEAE-cellulose-exchange chromatography may be used. In addition, affinity chromatography such as affi-blue gel affinity chromatography could be used at this step.

c) Protein separation based on hydrogen bonding, for example, using hydrophobic interaction chromatography.

d) Protein separation based on carboxyl and amino charges, for example, anion exchange chromatography or electrophoresis.

e) Separating substances based upon their weakly polar or non-polar moieties using ion-exchange chromatography using reverse-phase HPLC.

In particular, the following methods and materials were found to be particularly useful: (1) ammonium sulfate precipitation, (2) chromatography over controlled-pore glass beads, (3) hydrophobic interaction chromatography using a silica-phenyl matrix, (4) anion exchange chromatography using a silica-DEAE matrix, and (5) reverse-phase HPLC using a silica-alkyl (C4) matrix.

Also contemplated by the present invention are purified INHIB fragments or its derivatives manufactured using organic synthesis or recombinant DNA techniques, or by proteolysis.

It will be appreciated by those of skill in the art that other purification steps may be substituted for the preferred method described above. For example, instead of using chromatography over controlled-pore glass beads in step (b), one could equally use affi-blue gel chromatography to remove serum albumin from a serum sample containing INHIB. (See Travis et al., *Biochem. J.* 157:301-306 (1976); Yip et al., PNAS 78:1601).

By the term "mammal" is intended all mammals in which INHIB may be obtained from tissue or fluid and for which the inhibition of eosinophilic or neutrophilic immunologic activity, for example, and other uses of the present invention, described below, have a beneficial effect. Foremost among such mammals are humans; however, the invention is not intended to be so limiting, it being within the contemplation of the invention to treat any and all mammals which may experience the beneficial effects of the invention.

The present invention also includes methods of detecting INHIB or its functional derivatives in a sample or subject. For example, antibodies specific for INHIB, or its functional derivatives, may be detectably labeled with any appropriate ligand, for example, a radioisotope, an enzyme, a fluorescent label, a paramagnetic label, or a free radical. The presence of inflammation may be detected through the use of such detectably labeled materials. Methods of making and detecting such detectably labeled antibodies or their functional derivatives are well known to those of ordinary skill in the art.

The term "antibody" refers to monoclonal or monospecific antibodies which have a substantially homogeneous population of molecules. Monoclonal antibodies directed toward INHIB may be obtained by methods known to those skilled in the art. See, for example, Kohler and Milstein, *Nature* 256:495-497 (1975) and U.S. Pat. No. 4,376,110. These publications, as well as those mentioned hereunder, are incorporated herein by reference. Unless defined otherwise, various terms used herein have the same meaning as is well understood in the art to which the invention belongs.

The term "antibody" is also meant as well to include both intact molecules as well as fragments thereof, such as, for example, Fab and $F(ab')_2$, which are capable of binding to antigen.

It is possible to use antibodies, or their functional derivatives, to detect or diagnose the presence and location of an inflammation in a mammalian subject suspected of having an inflammation by utilizing an assay for INHIB, comprising incubating a biological sample from said subject suspected of containing INHIB in the presence of a detectably labeled binding molecule (e.g., antibody) capable of identifying INHIB, and detecting said binding molecule which is bound in a sample.

Thus, in this aspect of the invention, a biological sample may be treated with nitrocellulose, or other solid support which is capable of immobilizing cells, cell particles or soluble protein. The support may then be washed with suitable buffers followed by treatment with the detectably labeled INHIB-specific antibody. The solid phase support may then be washed with the buffer a second time to remove unbound antibody. The amount of bound label on the antibody may then be detected by conventional means.

One embodiment for carrying out the assay of the present invention on a sample containing INHIB, comprises:

(a) separating INHIB from the sample;

(b) contacting the separated INHIB with a solid support to effect immobilization of INHIB;

(c) contacting said solid support with a detectably labeled INHIB-specific antibody;

(d) incubating said detectably labeled INHIB-specific antibody with said support for a time sufficient to allow the INHIB-specific antibody to bind to the immobilized INHIB;

(e) separating the solid phase support from the incubation mixture obtained in step (d); and (f) detecting the bound label and thereby detecting and quantifying INHIB.

This aspect of the invention relates to a method for detecting INHIB or fragment thereof in a sample comprising (a) separating INHIB from the sample;

(b) contacting the separated INHIB with an INHIB-specific antibody or fragment thereof which binds to INHIB; and (c) detecting whether a complex is formed.

Of course, the specific concentrations of detectably labeled antibody and INHIB, the temperature and time of incubation, as well as other assay conditions may be varied, depending on various factors including the concentration of INHIB in the sample, the nature of the sample, and the like. The binding activity of a given lot of antibody directed toward INHIB may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the INHIB-specific antibody can be detectably labeled is by linking the same to an enzyme. This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the INHIB-specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The INHIB-specific antibody may also be labeled with a radioactive isotope which can be determined by such means as the use of a gamma counter or a scintillation counter or by audioradiography. Isotopes which are particularly useful for the purpose of the present invention are: $^3H$, $^{125}I$, $^{131}I$, $^{35}S$, $^{14}C$, and $^{51}Cr$.

It is also possible to label the INHIB-specific antibody with a fluoroscent compound. When the fluoroscently labeled antibody is exposed to light of the proper wave length, its presence can then be detected due to the fluorescence of the dye. Among the most commonly used fluorescent labelling compounds are fluorescein isothiocyanate, rhodamine, phycoerythrin, phycocyanin, allophycocyanin, o-phthaldehyde and fluorescamine.

The INHIB-specific antibody can also be detectably labeled using fluorescence emitting metals such as $^{152}Eu$, or others of the lanthanide series. These metals can be attached to the INHIB-specific antibody using such metal chelating groups as diethylenetriaminepentaacetic acid (DTPA) or ethylenediaminetetraacetic acid (EDTA).

The INHIB-specific antibody also can be detectably labeled by coupling it to a chemiluminescent compound. The presence of the chemiluminescent-tagged INHIB-specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the INHIB-specific antobody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the INHIB-specific antibody may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

The detection of foci of such detectably labeled antibodies is indicative of a site of inflammation. In one embodiment, as described above, this examination for inflammation is accomplished by removing samples of tissue or blood and incubating such samples in the presence of detectably labeled antibodies. In a preferred embodiment, this technique is accomplished in a noninvasive manner through the use of magnetic imaging, fluorography, etc. For example, such a diagnostic test may be employed in monitoring organ transplant recipients for early signs of potential tissue rejection. Such assays may also be conducted in efforts to determine a subject's clinical status in rheumatoid arthritis and other chronic inflammatory diseases.

INHIB is involved in inflammatory processes. The term "inflammation" is meant to include reactions of both the specific and non-specific defense systems. A specific defense system reaction is a specific immune system reaction response to an antigen. Examples of a specific defense system reaction include the antibody response to antigens such as rubella virus, and delayed-type hypersensitivity response mediated by T-cells (as seen, for example, individuals who test "positive" in the Mantaux test).

A non-specific defense system reaction is an inflammatory response mediated by leukocytes incapable of immunological memory. Such cells include granulocytes, macrophages, neutrophils, eosinophils, etc. Examples of a non-specific defense system reaction include the immediate swelling at the site of a bee sting, the reddening and cellular infiltrate induced at the site of a burn, and the collection of polymorphonuclear (PMN) leukocytes at sites of bacterial infection (e.g., pulmonary infiltrates in bacterial pneumonia, pus formation in abscesses).

It will be appreciated that the present invention will be easily adapted to the diagnosis, monitoring, and treatment of inflammatory disease processes such as rheumatoid arthritis, acute and chronic inflammation, post-ischemic (reperfusion) leukocyte-mediated tissue damage, acute leukocyte-mediated lung injury (e.g., Adult Respiratory Distress Syndrome), and other tissue- or organ-specific forms of acute inflammation (e.g., glomerulonephritis).

The term "treatment" is meant to include the prevention, elimination and attenuation or amelioration of the conditions of pathology described below.

As would be apparent to one of ordinary skill in the art, the therapeutic effects of INHIB may be obtained by providing to a patient the entire INHIB molecule, or any therapeutically active peptide fragment thereof.

As is also apparent, the therapeutic advantages of INHIB may be augmented through the use of INHIB mutants or variants possessing additional amino acid residues added to enhance its coupling to a carrier or to enhance the activity of INHIB. The scope of the present invention is further intended to include mutant forms of INHIB (including INHIB molecules which lack certain amino acid residues, or which contain altered amino acid residues, so long as such mutant INHIB molecules exhibit the capacity to affect cellular function).

The INHIB molecule of the present invention and its functional derivatives can be formulated according to known methods of preparing pharmaceutically useful compositions, whereby these materials or their functional derivatives are combined in a mixture with a pharmaceutically acceptable carrier vehicle. The objects and advantages of the present invention may be achieved by such a composition comprising INHIB when administered in said suitable pharmaceutically acceptable (sterile and nontoxic) carrier to mammals suffering from inflammatory disease conditions, cancer, or the like. Suitable vehicles and their formulation are described, for example, in *Remington's Pharmaceutical Sciences* (16th ed., Osol, A., Ed., Mack, Easton, Pa. (1980)). In order to form a pharmaceutically acceptable composition suitable for effective administration, such compositions will contain a therapeutically effective amount of INHIB molecule, or its functional derivatives (an inflammation-reducing amount), together with a suitable amount of carrier vehicle.

As used herein, the preparations and compositions of the present invention mediate suppression of, attenuate, or ameliorate inflammation, if, when provided to an animals, their administration results in either a decrease in the inflammation or prevalence of inflammation-associated cells. It is to be understood that the compositions and preparations of the present invention are to be provided to an animal in amounts and at frequencies capable of successfully mediating the suppression of said inflammation. The proper amounts and frequencies will be readily discernable to those of skill in the art.

Compositions within the scope of this invention include all compositions wherein each of the components thereof is contained in an amount effective to achieve its intended purpose.

Suitable pharmaceutically acceptable carriers may comprise excipients and auxiliaries which facilitate processing of the active compounds into preparations which can be used pharmaceutically. These will be readily apparent to those of skill in the art.

A preferred product of the invention is a sterile pharmaceutical composition for therapeutic use containing INHIB or its functional derivatives, which is suitable for intravenous administration. The product may be in lyophilized form to be reconstituted for use by addition of a suitable carrier, or diluent, or it may be in the form of an aqueous solution.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

As mentioned above, the products of the invention may be incorporated into pharmaceutical preparations which may be used for therapeutic purposes. However, the term "pharmaceutical preparation" is intended in a broader sense herein to include preparations containing a protein composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of INHIB, i.e., that amount necessary for preventative or curative health measures. If the pharmaceutical preparation is to be employed as a reagent or diagnostic, then it should contain reagent or diagnostic amounts of INHIB.

A composition is said to be "pharmaceutically acceptable" if its administration can be tolerated by a recipient patient. Such an agent is said to be administered in a "therapeutically effective amount" if the amount administered is physiologically significant. An agent is "physiologically significant" if its presence results in a detectable change in the physiology of a recipient patient.

By definition, one unit of INHIB or free $\beta$ chain activity will produce 50% inhibition of cytokine-activated eosinophil cytotoxicity or neutrophil adherence at an eosinophil concentration of $2 \times 10^6$ cells/ml and a neutrophil concentration of $2 \times 10^6$ cells/ml in a standardized in vitro assay system. INHIB at a concentration of 20 U/ml produces a maximal inhibition of 100% at the same cell concentration.

The therapeutic and/or diagnostic dosage administered will be dependent upon the particular inflammatory condition involved and may be dependent upon the age, weight, height, sex, general medical condition, and kind of concurrent treatment, if any, of the mammalian subject.

Methods useful for administering the molecules of the present invention include topical, subcutaneous, intraarticular, intraperitoneal, intrapleural, or intraocular. When administering INHIB or its functional derivatives by injection, the administration may be by continuous infusion, or by single or multiple boluses.

The effective molecule useful in the methods of the present invention may be employed in such forms as, for example, sterile suspensions for injection or encapsulated for targeting to specific tissue sites with antibodies directed to inflammation-related cell surface structures.

Additional pharmaceutical methods may be employed to control the duration of action. Controlled release preparations may be achieved through the use of polymers to complex or absorb INHIB or its functional derivatives. The controlled delivery may be achieved by selecting appropriate macromolecules (for example, polyesters, polyamino acids, polyvinyl, pyrrolidone, ethylenevinylacetate, methylcellulose, carboxymethylcellulose, or protamine, sulfate) and the appropriate concentration of macromolecules as well as the methods of incorporation, in order to control release.

Another possible method useful in controlling the duration of action by controlled release preparations is incorporation of the INHIB molecule or its functional derivatives into particles of a polymeric material such as polyesters, polyamino acids, hydrogels, poly(lactic acid), or ethylene vinyl acetate copolymers.

Alternatively, instead of incorporating INHIB or its functional derivatives into polymeric particles, it is possible to entrap these materials in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nanoparticles, and nanocapsules), or in macroemulsions. Such techniques are disclosed in *Remington's Pharmaceutical Sciences* (1980).

One other method useful in controlling inflammation concerns the administration of a pharmaceutical preparation which includes the known free $\beta$ chain of complement C3. C3 has a number of well-characterized cleavage products that enhance leukocyte function in the development of inflammation (Ross et al., *Adv. Immunol.* 37:217 (1985); Müller-Eberhard, In *Inflammation*, Gallin et al., editors, Raven Press, N.Y. (1985)), but there has been no evidence of a function for free $\beta$ chain or that C3 related substances can suppress the function of inflammatory cells. As shown in the following Examples, dose dependent suppression of eosinophil cytotoxicity and neutrophil adherence functions demonstrates, unexpectedly, that the free β chain of C3 is capable of inhibiting inflammation.

Purified INHIB can be employed as a therapeutic agent in immunologic disease in mammals, particularly diseases in which suppression of inflammation would be helpful. For example, purified INHIB may be employed for the treatment of cancers, viral and other infectious diseases, autoimmune diseases, for the correction of immune-deficiency diseases, and the like. Purified INHIB could be used to generate antibodies as described, and to predict the structure of oligonucleotide probes; these reagents could be used to screen cDNA libraries for the isolation of the gene encoding INHIB. The purification method, or some of its components, could be used on a larger scale for the purification of biosynthetic (recombinant) INHIB.

Understanding the processes by which INHIB inhibits cytokine-activated leukocyte immunologic activity, such as eosinophil cytotoxicity and neutrophil adherence, will aid in the development of its therapeutic and/or diagnostic uses in the fields of organ transplantation, allergy, and oncology, for example. This invention will enable those in the medical field to more effectively diagnose and treat inflammatory disease processes, and to utilize a quantitative assay for INHIB in order to monitor the time-course and/or intensity of ongoing clinical episodes of inflammation. The invention will further enable researchers to investigate mechanisms of eosinophil and neutrophil interactions with other cells and eosinophil and neutrophil function in inflammation.

Having now fully described the present invention, the same will be more clearly understood by reference to certain specific examples which are included herewith for purposes of illustration only and are not intended to be limiting of the invention, unless specified.

EXAMPLES

Cytokines. Recombinant human tumor necrosis factor (TNF), produced by *E. coli* and purified by the method of Wang et al., *Science* 228:149 (1985), was provided by Cetus Corporation. Unless otherwise specified, TNF was used at a concentration of 100 U/ml, the optimal dose for the eosinophil cytotoxicity assay (Silberstein et al., *Proc. Natl. Acad. Sci. USA* 83:1055 (1986). For some experiments, purified monoclonal antibody 245-10E11 (Fendly et al., *Hybridoma* 6:359 (1987)) was used to neutralize the activity of TNF. The neutralizing titer of the antibody was determined by the L929 cell cytotoxicity assay (Wang et al., *Science* 228:149 (1985)). Recombinant human granulocyte-macrophage colony-stimulating factor (GM-CSF), produced by COS cells and purified, was provided by Dr. Judith C. Gasson. GM-CSF was used at a final concentration of 20 pM, the optimal dose in the eosinophil cytotoxicity assay (Silberstein et al., *J. Immunol.* 137:3290 (1986)).

Purified TNF was radioiodinated using IODO-BEADS (Pierce Chemical Co.). Autoradiography of $^{125}$I-TNF following SDS-PAGE showed that the iodinated protein and the unlabeled TNF migrated in the same fashion. The majority (50–100%) of the initial bioactivity was recovered, as determined by the L929 cytotoxicity assay (Wang et al., *Science* 228:149 (1985)). The specific activity of the labeled TNF was $0.7-7 \times 10^8$ cpm/'g (0.71-7.1 mCi/'M).

Blood donors. Venous blood was obtained from laboratory personnel for the preparation of serum, eosinophils and neutrophils. Some of the donors for eosinophil studies had moderately elevated eosinophil counts in association with allergies and/or asthma (total eosinophil counts ranged from 1 to 18% of total leukocytes for these studies). A human subject (NR) was identified whose eosinophils and neutrophils were uniquely (in a study population of 38) unresponsive to TNF in immunological assays in vitro. Serum from this subject and 5 of 122 other subjects tested, inhibited eosinophil cytotoxic function in a dose-dependent manner.

Figure 7:
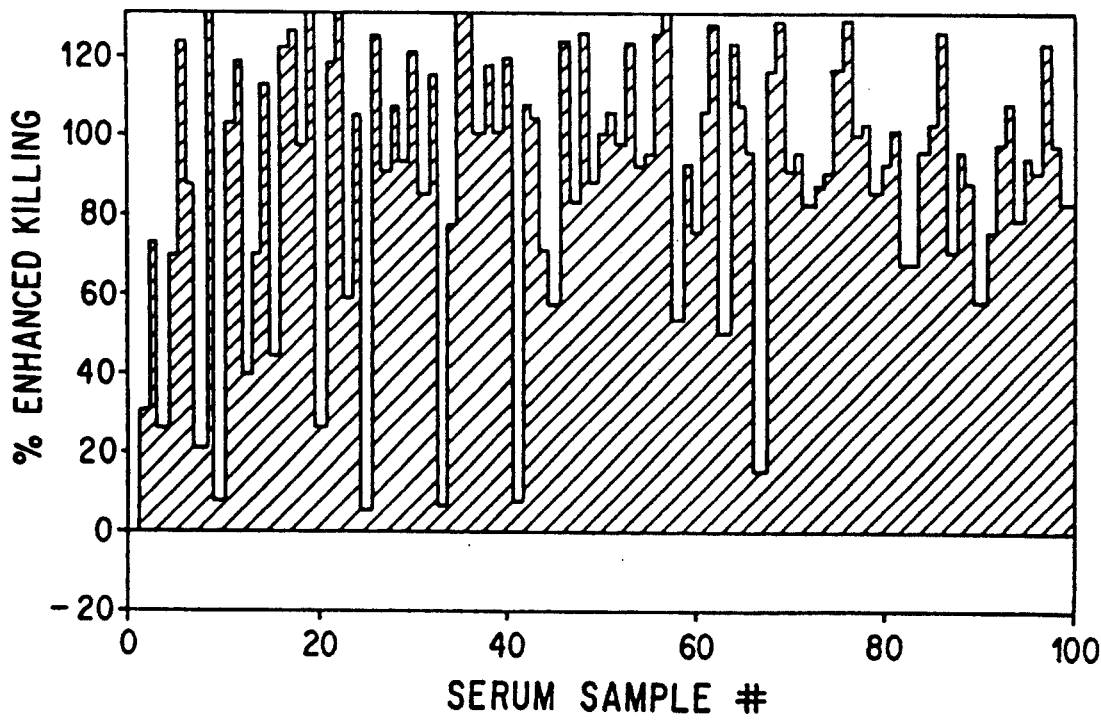
FIG. 7. Population distribution of the inhibitory activity in human sera. 100 anonymous serum samples were obtained from the Red Cross and tested as in FIG. 6 for the ability to inhibit the cytotoxic function of TNF-activated eosinophils at a concentration of 10%.
Figure 8A:
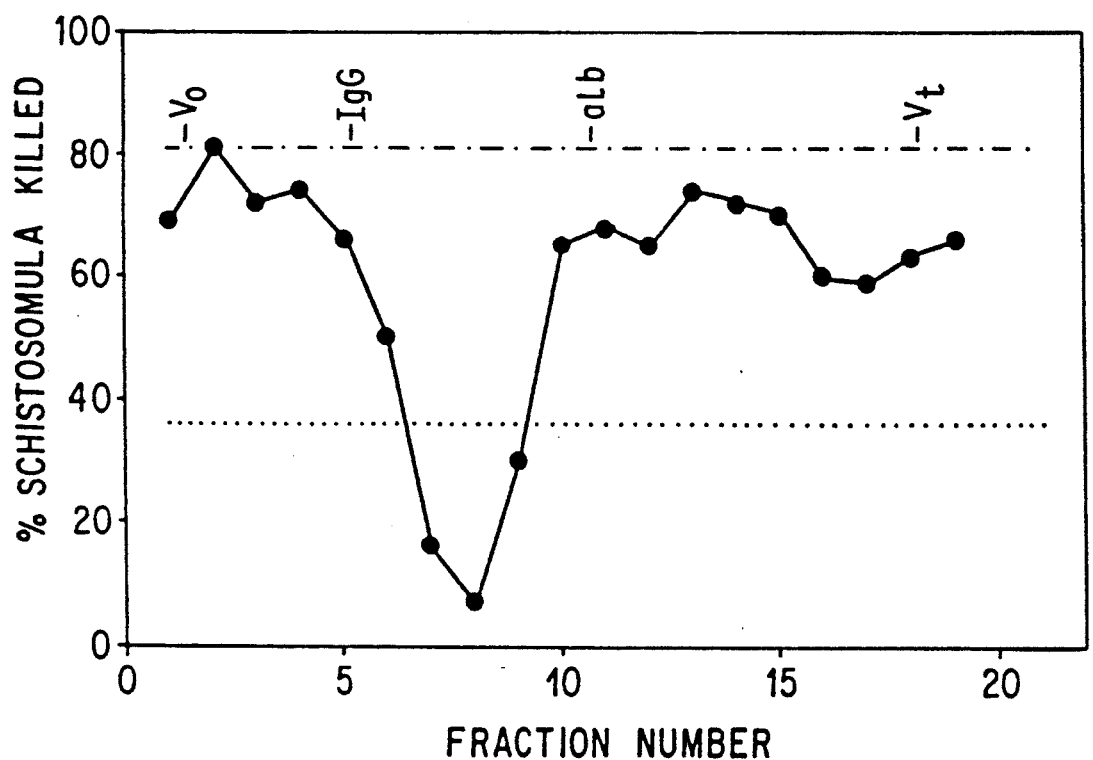
FIGS. 8A and B. HPLC sizing analysis of INHIB.
Figure 8B:
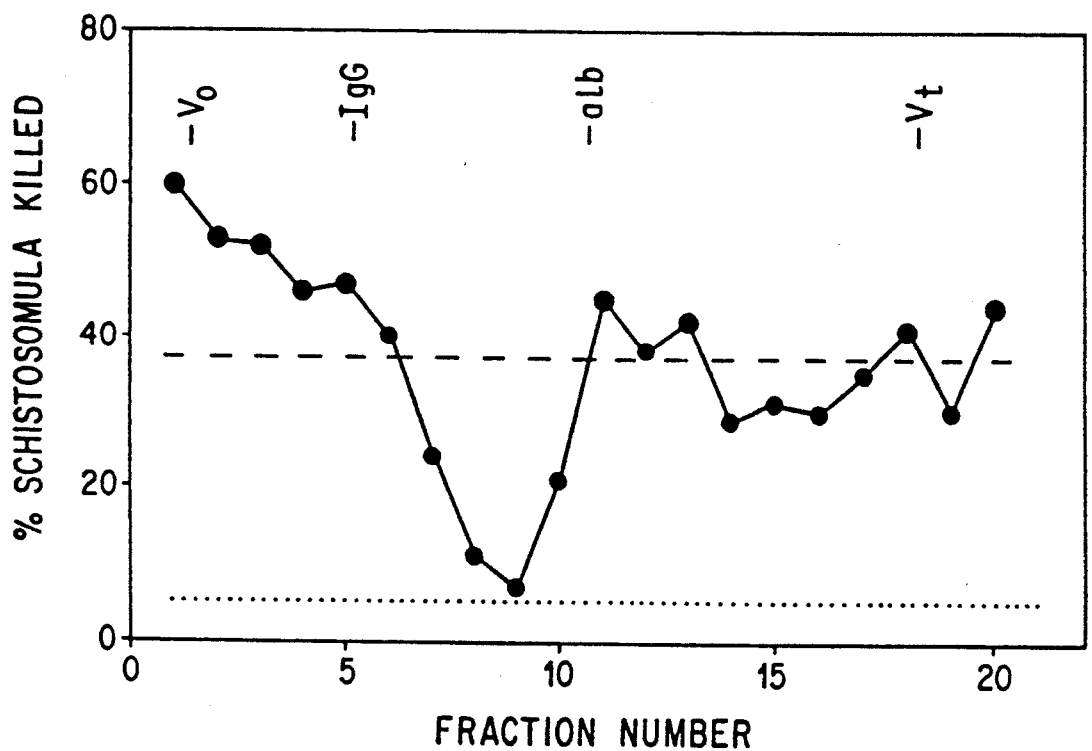
FIG. 8(B). Emergence of INHIB activity when normal serum is chromatographed. The conditions of chromatography and bioassay were as for A.
Figure 9A:
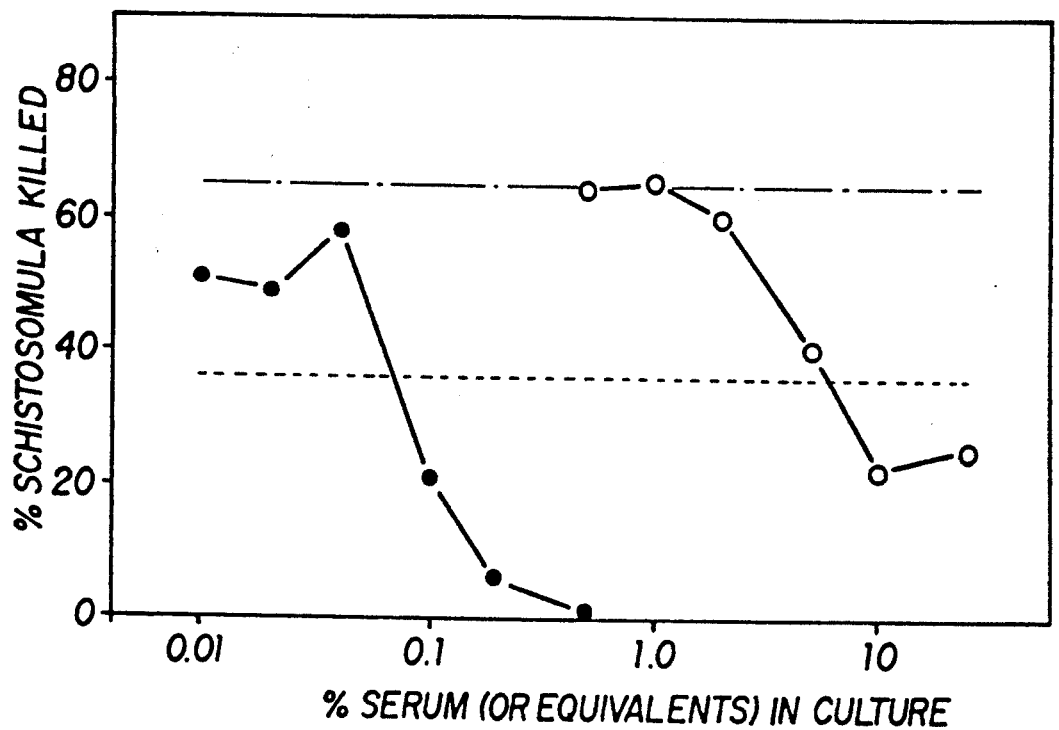
FIGS. 9A, 9B and 9C. Increase in the titer of INHIB as a consequence of HPLC sizing chromatography. NR serum (FIG. 9A, same sample as FIG. 8A), a human serum pool (lot 29309039, obtained from Flow Laboratories) (FIG. 9B), a control serum sample with no inhibitory activity (FIG. 9C, same sample as FIG. 8B), and HPLC fractions 7 through 9 of these sera were tested for inhibitory activity in the eosinophil cytotoxicity assay at the indicated concentrations.
Figure 9B:
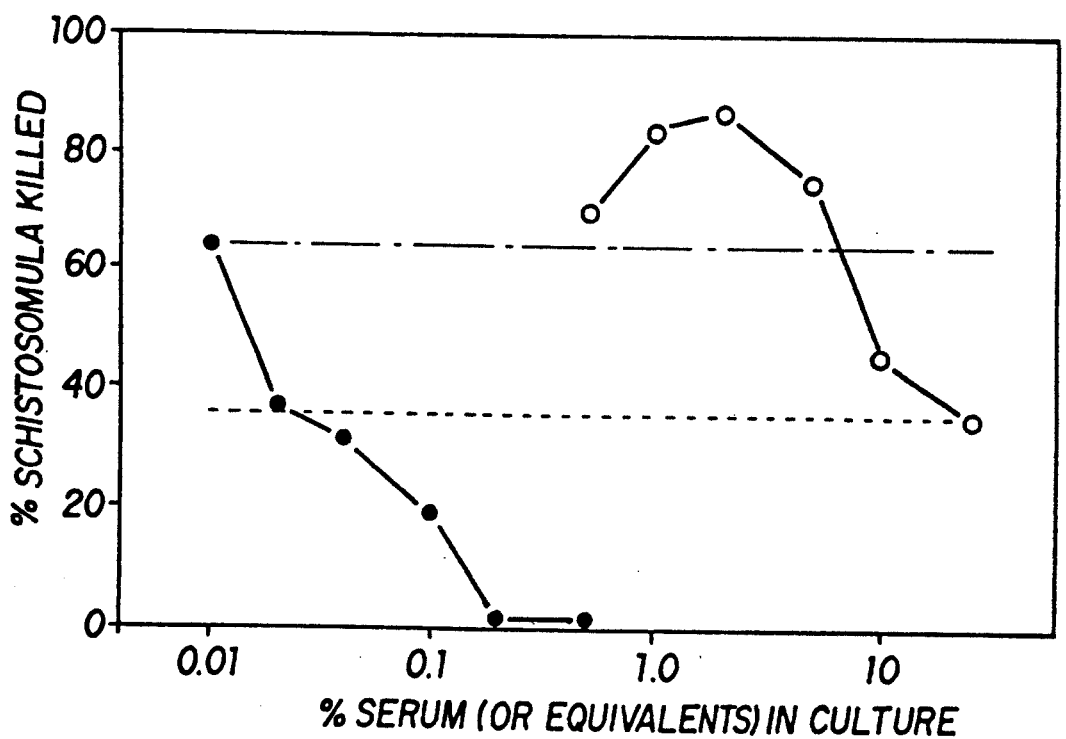
Figure 9C:
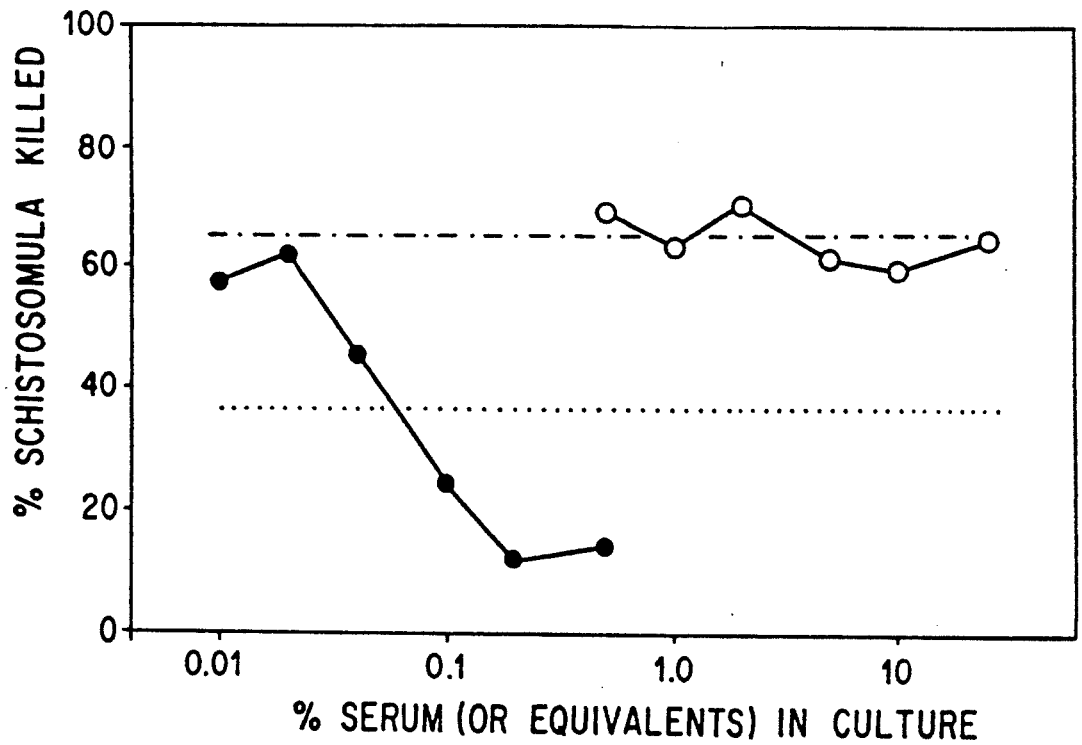
Figure 10:
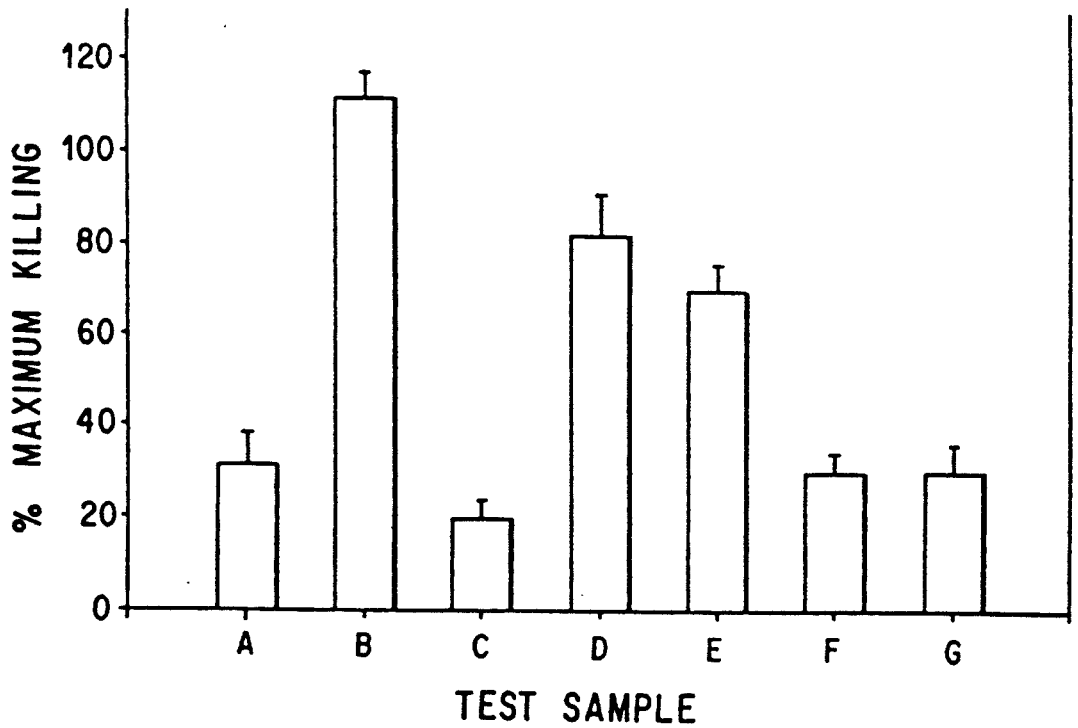
FIG. 10. Sensitivity of INHIB to heat or trypsin treatment. The results in 3 experiments with INHIB from NR serum and 4 experiments with different control sera were essentially similar; in order to compare the results on the same scale, the level of killing in the presence of TNF with no inhibitors present was set equal to 100%. Values represent the mean % maximum killing±S.E. in 7 experiments. Killing was assayed under standard conditions when eosinophils were stimulated with: A, control medium; B, TNF plus 1% trypsin (2×0.5% trypsin w/z at 37° C. for 30 minutes) plus soybean trypsin inhibitor (4-fold excess neutralizing units); C, TNF plus untreated INHIB; D, TNF plus treated INHIB (treatment=80° C. for 1 hour); E, TNF plus INHIB (1 hour trypsin, then SBTI);F, TNF plus INHIB (1 hour SBTI and trysin); G, sample E with fresh INHIB added at end.

One hundred anonymous serum samples were also supplied by the American Red Cross Blood Services, Northeast Region (Dedham, Mass.; for use in a studies related to FIG. 7 and Table 1.

Antibody. Antibody to schistosomula of the human blood fluke *S. mansoni* was obtained from Brazilian schistosomiasis patients, as described previously (Silberstein et al., *Proc. Natl. Acad. Sci. USA* 83:1055 (1986)).

EXAMPLE ONE

Preparation of Serum, Eosinophils, and Neutrophils

Blood for the preparation of serum was collected in glass tubes, incubated at 37° C. for 1 hour and then overnight at 4° C. The serum was clarified by centrifugation and stored frozen at −20° C.

Heparinized blood for the preparation of eosinophils was processed by a sequence of dextran sedimentation and discontinuous metrizamide density gradient centrifugation (Vadas et al., *J. Immunol.* 122:1228 (1979)). The purity of eosinophil preparations, as evaluated by examination of Wright's-Giemsa stained slides, ranged from 80 to 99%.

Heparinized blood for the preparation of neutrophils was processed by a sequence of dextran sedimentation and Ficoll-Hypaque centrifugation (Boyum et al. *Scand. J. Clin. Lab. Invest.* 21 (Suppl. 97):77 (1968)). Erythrocytes were removed by hypotonic lysis. The neutrophil preparations were essentially free of mononuclear cells and contained < 10% eosinophils.

EXAMPLE TWO

Assay of Eosinophil Cytotoxic Function

Eosinophils were washed two times and suspended at a concentration of $2 \times 10^6$/ml in assay medium (minimal essential medium with Earle's salts, supplemented with 25 mM HEPES, 2 mM glutamine, 100 U/ml penicillin G, 100 μg/ml streptomycin, and 10% heat-inactivated fetal calf serum, all from GIBCO, Grand Island, N.Y.).

Mechanically-transformed schistosomula of *Schistosoma mansoni* were prepared as described previously (Ramalho-Pinto et al., *Exp. Parasitol.* 36:360 (1974)), washed four times, and suspended at a concentration of 2000/ml in assay medium. Cytokines, heat-inactivated anti-schistosomula serum, and test inhibitor were diluted to five times the final concentration in assay medium. Unless otherwise specified, 50 μl each of cytokine (or control medium), inhibitor (or control medium), and eosinophils, were added to wells of a tissue culture plate (96-well, round-bottomed). Some experiments that did not involve the study of inhibitors, were done using final volumes of 200 μl, with four-times concentrated stocks of cytokine and antibody.

The plates were incubated for 30 minutes at 37° C. in a sealed, humidified box. After this period, 50 ul each of antibody and schistosomula were added, and the plates were incubated at 37° C. in a sealed, humidified box. For experiments in which the inhibitor was removed, the contents of microwells were transferred to 12×75 mm polypropylene tubes, diluted with 5 ml of medium, and centrifuged at 500 g for 5 minutes. The supernatant was aspirated, and the eosinophils and schistosomula in the pellet were recultured in 250 μl of assay medium with fresh inhibitor and cytokine.

The killing of schistosomula was scored by microscopy at approximately 40 hours, using uptake of toluidine blue and lack of motility as indications of death. The death of cultured schistosomula was negligible when either antibody or eosinophils was absent from the cultures.

TABLE ONE

Irreversibility of the Activation of INHIB
% Reduction in TNF-Enhanced Cytotoxic Function(a)

| % Inhibitor | Serum(b) | INHIB(c) | INHIB + Serum(d) |
|---|---|---|---|
| 20 | 0 | 100 | 97 |
| 10 | 4 | 54 | 73 |
| 5 | 0 | 35 | 0 |
| 2.5 | 0 | 0 | 0 |
| 1.2 | 0 | 3 | 0 |

(a)% decrease in TNF-enhanced killing of schistosomula; 37% killed by TNF-stimulated eosinophils (0% decrease); 5% killed by unstimulated eosinophils (100% decrease).
(b)serum from a control subject with no inhibitory activity.
(c)pooled fractions containing activated INHIB, prepared by HPLC sizing chromatography (dilution factor = 50 with respect to serum, due to chromatography and pooling of fractions).
(d)the indicated concentration of INHIB added to an equal volume of the serum from which it was derived.

EXAMPLE THREE

Assay of Neutrophil Function

The ability of neutrophils to kill schistosomula was assayed as for eosinophils, except that an effector to target ratio of 5000:1 was used.

To determine neutrophil adherence to plastic, neutrophils were suspended at a concentration of $10^5$ cells/200 μl of assay medium in the presence or absence of 100 U/ml TNF and allowed to settle in round-bottomed microtiter wells at 37° C. for 2 hours. After this period, the adherence of neutrophils to the plastic surface was assayed by one of two methods. As described previously (Silberstein et al., Proc. Natl. Acad. Sci. USA 83:1055 (1986); Arnaout et al., J. Clin. Invest. 78:597 (1986), the wells were examined using an inverted microscope. In the absence of TNF, there was very little adherence of neutrophils to the plastic, and most of the cells were in a pellet at the bottom of the wells. Usually, in the presence of TNF, neutrophils were seen covering the sides of the wells.

As an alternative method of measuring the adherence of neutrophils, non-adherent neutrophils were washed away with warm saline, and a solution containing 0.1% Triton X-100, 0.4 mM 2-2' azino-di-3-ethylbenzthiazoline-6-sulfonate plus 0.003% hydrogen peroxide in pH 4.0, 0.05M sodium citrate substrate was added to the wells. The generation of colored substrate (absorbance monitored at 405 nm) was dependent on the quantity of neutrophil myeloperoxidase in the wells.

Throughout the purification procedure there was strong correspondence between the ability of a test sample to suppress eosinophil cytotoxic function and its ability to suppress neutrophil adherence. Thus, purified INHIB is also able to suppress neutrophil functions and other leukocyte functions related to inflammation.

EXAMPLE FOUR

Measurement of Eosinophil and Neutrophil Production of $H_2O_2$

Production of $H_2O_2$ was measured by a modification of the method of Root et al. (J. Clin. Invest. 55:945 (1975)). Purified cells were washed and resuspended in buffer (4 mM sodium phosphate, pH 7.4, 128 mM sodium chloride, 12 mM potassium chloride, 1 mM calcium chloride, 2 mM magnesium chloride, and 2 mM glucose) at a concentration of $10^6$/ml. The cells were then placed in a cuvette (10×10×48 mm acrylic, Sarstedt, Princeton, N.J.) with 5 ul of horseradish peroxidase stock (6.25 mg/ml buffer, Sigma), 10 ul of scopoletin stock (1 mM in buffer, Sigma), 10 ul of control buffer or TNF (for some experiments), and maintained at 37° C. Fluorescence was monitored at 460 nm (with excitation at 350 nm) by a Perkin-Elmer model MPF-44B fluorescent spectrophotometer (Perkin-Elmer, Norwalk, Conn. When baseline fluorescence had been established for 5 minutes, the cells were stimulated either with 10 ul of phorbol myristate acetate (1 mg/ml in ethanol) or with IgG aggregates. The decrease in fluorescence, which is proportional to the production of $H_2O_2$, was recorded by a Perkin-Elmer model 056-1001 recorder.

IgG aggregates were prepared by known methods. Chromatographically purified human IgG (Organon Teknika-Cappel) was dissolved in $H_2O_2$ assay buffer at a concentration of 10 mg/ml. This solution was heated in a water bath at 62° C. for 25 minutes. Control preparations of IgG that were not heat-aggregated did not stimulate detectable production of $H_2O_2$ by eosinophils or neutrophils.

EXAMPLE FIVE

Assay Of The Biological Activity of TNF

The biological activity (expressed in units) of TNF was assayed as described (Wang et al., Science 228:149 (1985)), using the TNF-sensitive L929 cell line. The cells were cultured either with 1 μg/ml actinomycin D for 16 hours (seeded initially at $10^5$ cells/microwell) or without actinomycin D for 28 hours (seeded originally at $2\times10^4$ cells/-microwell). The viability of L929 cells was determined by the spectrophotometric measurement of the reduction of the tetrazolium salt MTT 3-(4,5-dimethylthiazol-2-)-2,5-diphenyl tetrazolium bromide to formazan by the mitochondrial enzyme succinate dehydrogenase, a reaction which occurs only in living cells (Denizot et al., J. Immunol. Meth. 89:271 (1986)).

EXAMPLE SIX

Measurement of Neutrophil Surface Membrane Receptors for TNF

Neutrophils were incubated overnight at 4° C. in Hank's balanced salt solution plus 1% sucrose in the presence of various doses of $^{125}I$-labeled TNF in the presence or absence of a 1000-fold excess of unlabeled TNF, as described previously (Creasey et al., PNAS USA 84:3293 (1987)). After this period, the neutrophils were washed in cold buffer, and the bound radiolabel was counted. Non-specific binding (radiolabel bound in the presence of unlabeled TNF) was subtracted from total bound radiolabel (in the absence of unlabeled TNF) to calculate specific binding.

EXAMPLE SEVEN

HPLC Sizing Analysis

100 μl samples of serum were chromatographed on the following HPLC sizing columns: TSK-250 and TSK-4000 BioSil 7×600 mm columns (BioRad, Richmond, Calif.) and a Zorbax G-250 column (Dupont, Wilmington, Del.). The chromatography solvent consisted of 0.9% sodium chloride, 25 mM HEPES at pH 7.0, 100 U/ml penicillin G, and 100 ug/ml of streptomycin. The molecular weight of the inhibitory component (INHIB) was estimated by size exclusion HPLC at 80 to 100 kilodaltons (kD). When control serum samples with no detectable INHIB were chromatographed in the same manner, INHIB of the same apparent molecular weight was detected. Partial purification of INHIB by molecular sizing HPLC increased the potency of INHIB.

In order to discover the population distribution of the inhibitory activity identified in NR serum, 22 sera from lab personnel and 100 anonymous sera from the Red Cross were tested in the eosinophil cytotoxicity assay. Eleven of these sera reduced TNF-enhanced killing of targets by >50% and 4 sera reduced TNF-enhanced killing by >90% (data not shown). The inhibitor was also detectable in a sample of pooled human type AB serum, that was obtained from Flow Laboratories (lot #29309039).

EXAMPLE EIGHT

The Purification of INHIB from Human Serum

Figure 15:
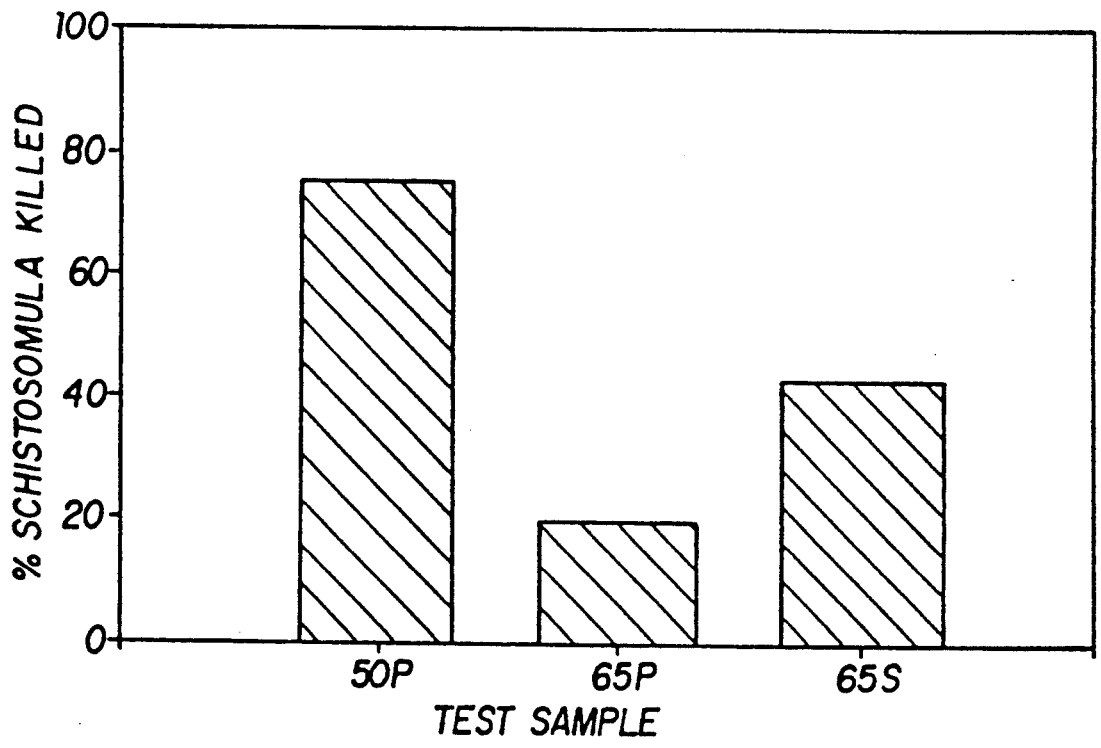
FIG. 15. Enrichment of INHIB by ammonium sulfate precipitation. Fractions of serum were generated as described in the text, dialyzed in medium, and tested in the eosinophil cytotoxicity assay, as described for FIG. 12.

Volumes up to 350 ml of human serum, either pooled or from a single donor, were processed for purification of INHIB by the following steps:

1. Ammonium sulfate precipitation: Serum was brought to 50% saturation with ammonium sulfate (29.1 g/100 ml) and mixed for 24 to 48 hours at 4° C. The slurry was centrifuged at approximately 10,000× g for 15 minutes. The resulting pellet (50P) was saved. The supernatant (50S) was brought to 65% saturation (addition of 9.2 g ammonium sulfate/100 ml). This was mixed in the cold and centrifuged as before. The resulting supernatant (65S) was saved. The pellet (65P) contained INHIB (FIG. 15), and was dialyzed in phosphate-buffered saline (PBS) for the next purification step.

Figure 16:
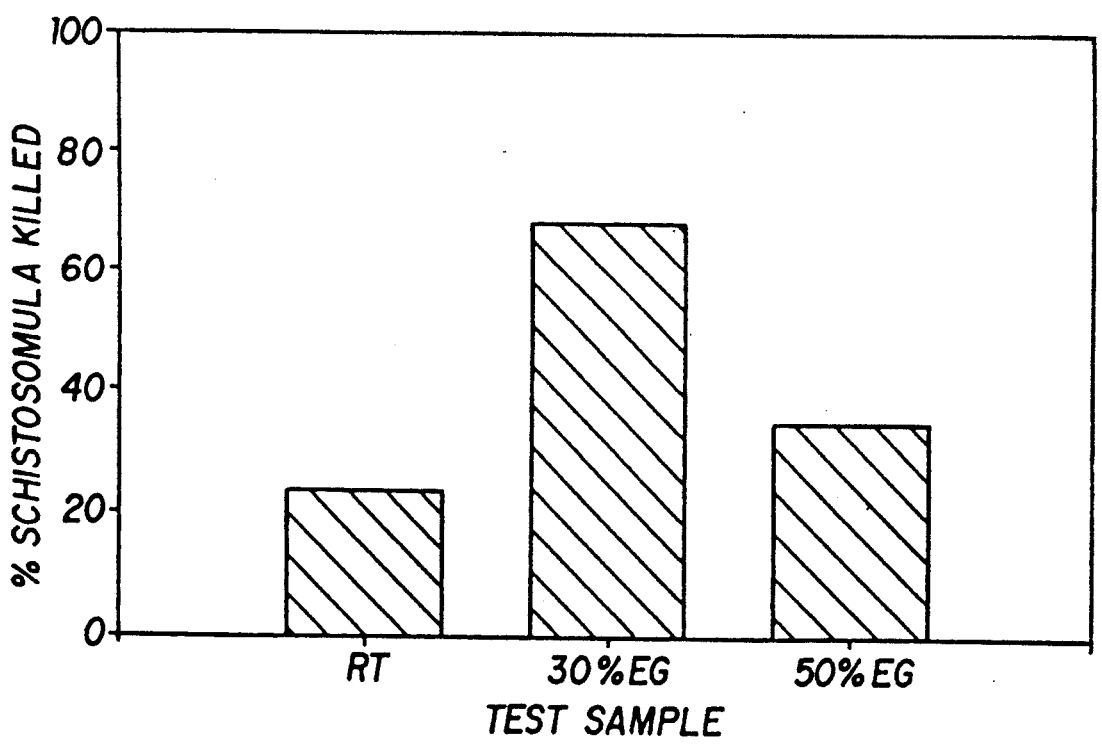
FIG. 16. Enrichment of INHIB by chromatography over controlled-pore glass beads. Samples were generated as described in the text and assayed as described for FIG. 12. The non-adherent run through (RT) usually contained some INHIB and could be recycled through the column.

2. Chromatography over controlled-pore glass beads: The 65P fraction was dissolved in PBS+0.04% sodium azide, dialyzed in more PBS, and diluted in PBS to 10 times the original volume of serum. This solution was mixed with controlled-pore glass beads (CPG Inc., Fairfield, N.J.) at a ratio of 1 g beads: 10 ml diluted 65P, overnight at 4° C. The beads were packed in a column with a height to width ratio of >50:1, washed with PBS, and eluted with 30% and then 50% ethylene glycol. INHIB was recovered in the 50% eluate (FIG. 16).

Figure 17A:
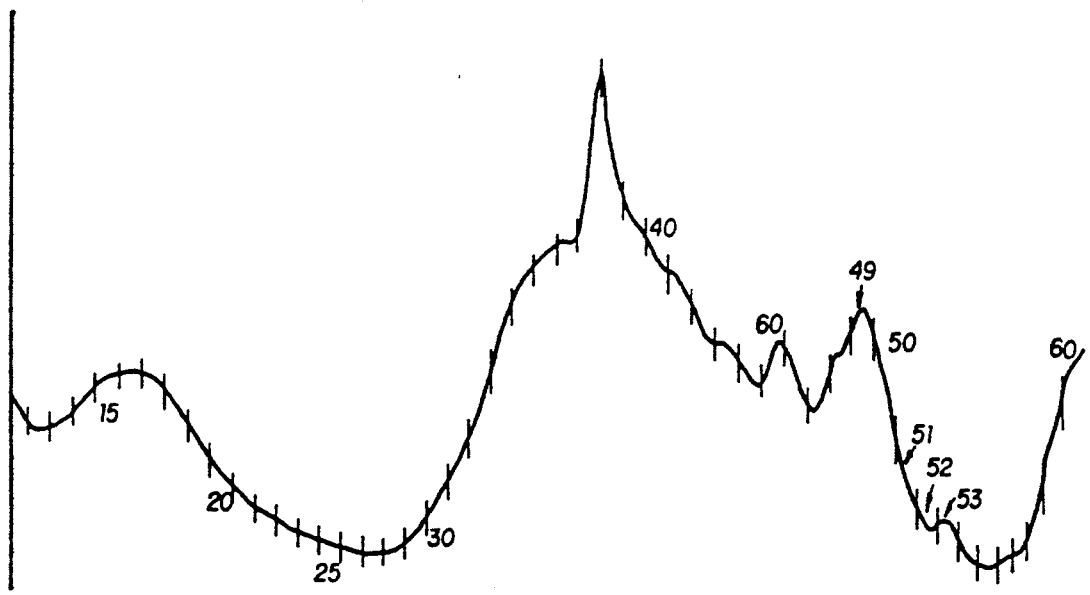
FIGS. 17A and 17B. Enrichment of INHIB by hydrophobic interaction chromatography. The active fraction from FIG. 16 was chromatographed as described in the text. The elution of proteins was monitored by absorbance at 280 nm (FIG. 17A, fraction numbers indicated). After dialysis in medium, aliquots of these fractions were tested in the eosinophil cytotoxicity assay, as described for FIG. 12 (FIG. 17B).
Figure 17B:
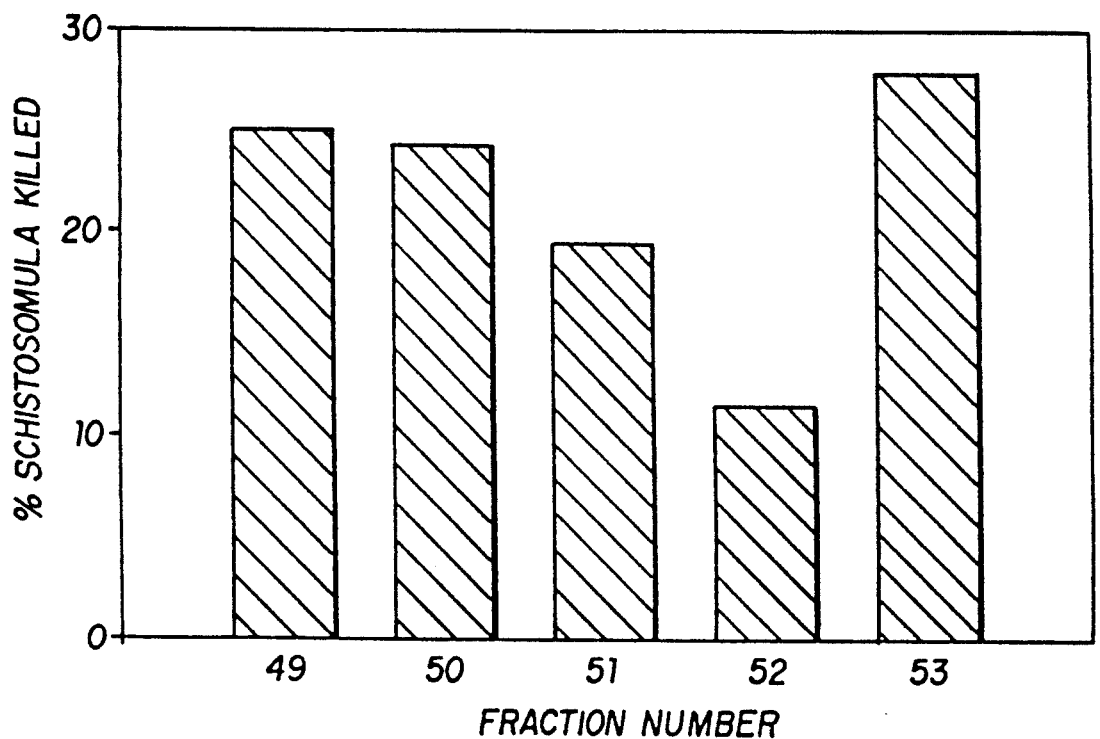

3. Hydrophobic interaction chromatography: The sample was dialyzed in buffer A (0.1M sodium phosphate, pH 7.0, plus 0.6M ammonium sulfate) and loaded on a Bio-Gel TSK-phenyl 5-PW HPLC column (75×7.5 mm, Bio-Rad, Richmond, Calif.) in the same buffer. The column was washed 15 minutes with buffer A and then eluted with a 45 minute gradient (flow=1 ml/minute) to buffer B (0.01M sodium phosphate, pH 7.0 plus 30% ethylene glycol). This was followed by a 15 minute wash with buffer B. INHIB was recovered in fraction 52 (1 minute fractions, beginning with injection) at approximately 25% solution B (FIG. 17B).

Figure 18A:
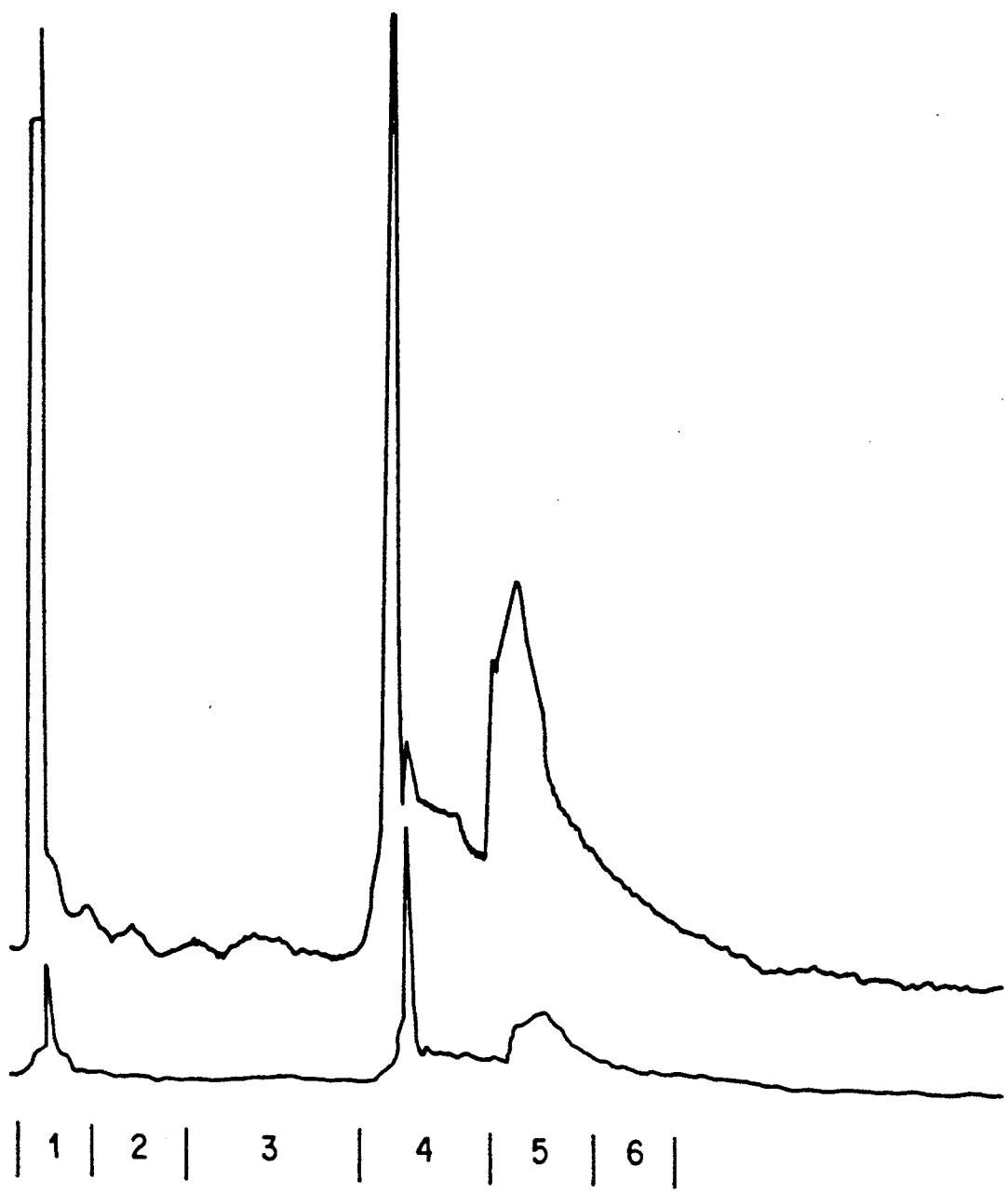
FIG. 18A and 18B. Enrichment of INHIB by anion exchange chromatography. The active fraction from FIG. 17B was chromatographed as described in the text. The elution profiles and biological activities were determined as described for FIGS. 17A and 17B. The elution profile of proteins at 280 nm is shown in FIG. 18A and results from the eosinophil cytotoxicity assay are shown in FIG. 18B.
Figure 18B:
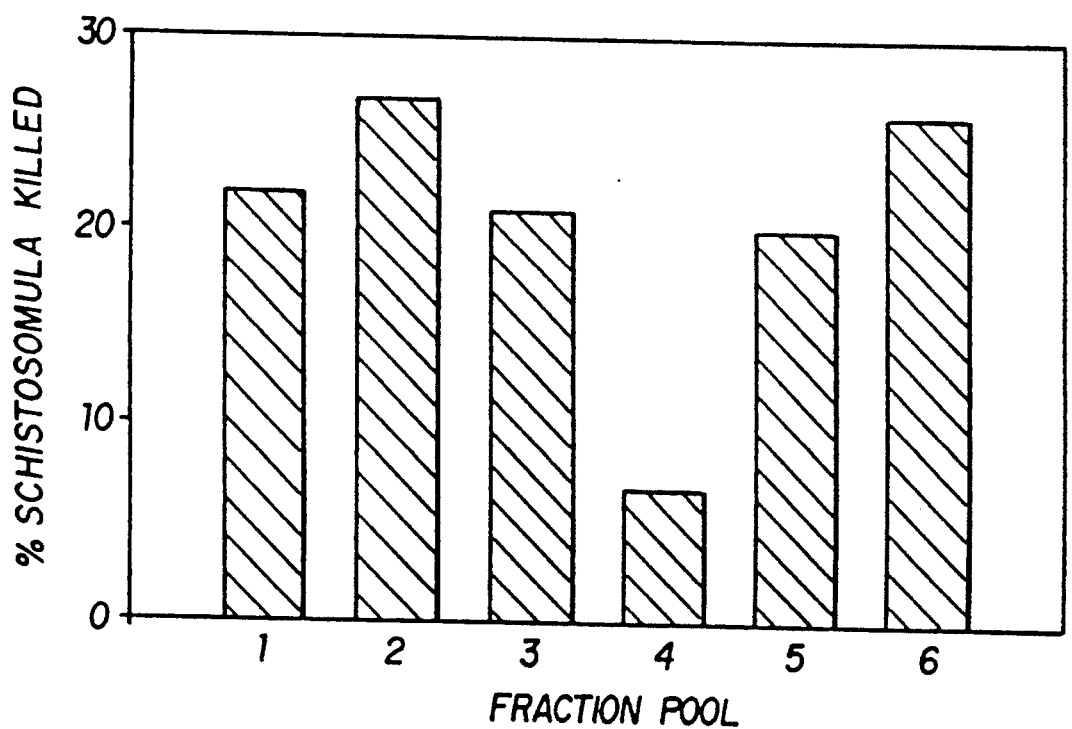

4. Anion exchange chromatography: The fraction was dialyzed in buffer C (0.02M Tris, pH 8.0) and loaded on a DEAE-5PW HPLC column (7.5×75 mm, Kratos, Ramsey, N.J.). The column was washed for 15 minutes with buffer C and eluted with a 30 minute gradient (flow=1 ml/minute) from buffer C to buffer D (0.02M Tris, pH 8.0 plus 0.5M ammonium sulfate). This was followed by a 15 minute wash with buffer D. INHIB was recovered in fraction pool 4 (FIG. 18B).

Figure 19A:
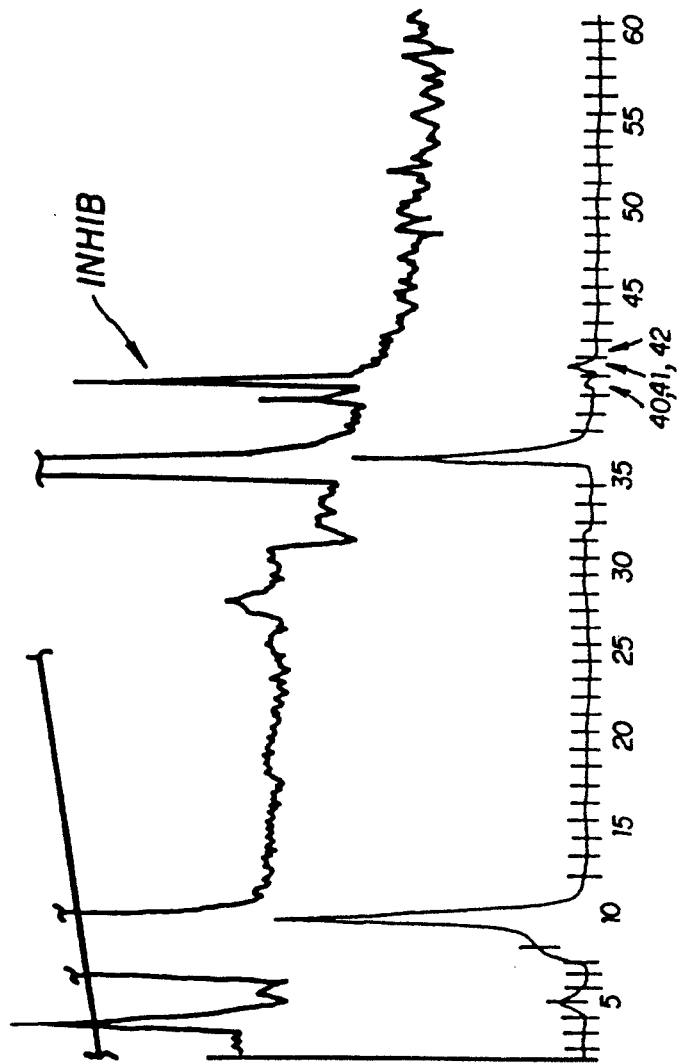
FIGS. 19A and 19B. Final purification of INHIB by reversed-phase HPLC. The active fraction from FIG. 18B was chromatographed as described in the text. The elution profiles and biological activities were determined as for FIGS. 17A and 17B, except that the results represent the mean of two experiments. The elution profile of proteins at 280 nm is shown in FIG. 19A. The range of 0–100% is equal to the difference between the negative control and the maximum killing. The arrow shows the peak of purified INHIB. The results of eosinophil cytotoxicity assays are shown in FIG. 19B.
Figure 19B:
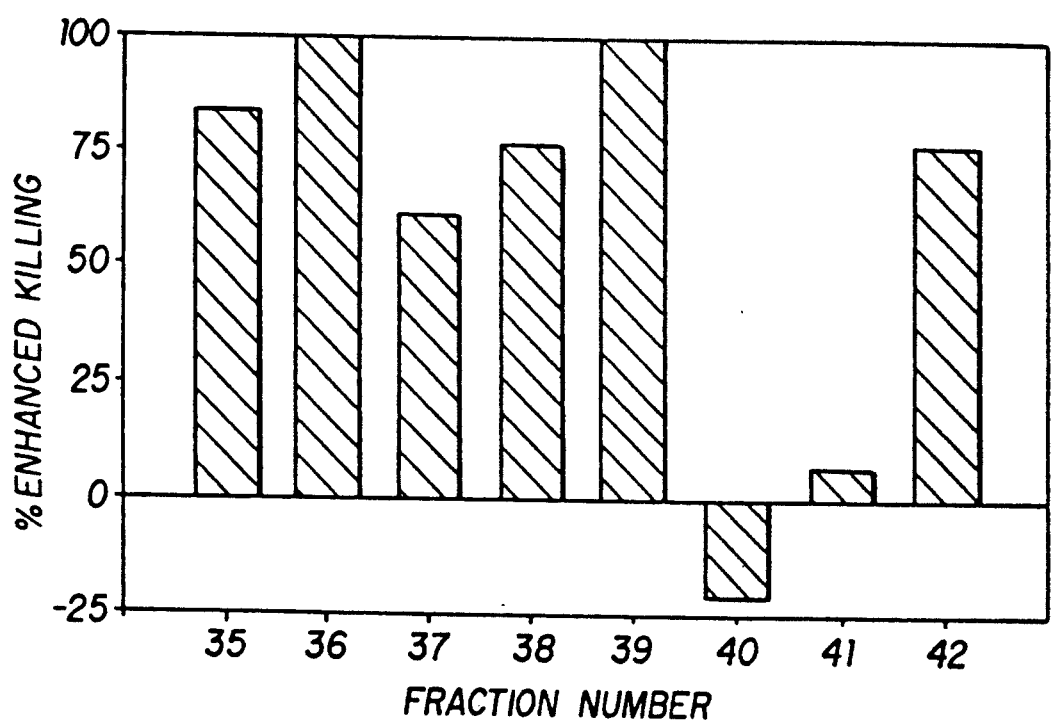

5. Reversed-phase HPLC: The pooled fractions were loaded on a Vydac C4 column (4.6×250 mm, the Nest Group, Southboro, Mass.). The column was washed with solution E (0.1% trifluoroacetic acid) for 20 minutes and eluted with a 30 minute gradient from solution E to solution F (0.1% trifluoroacetic acid plus 50% acetonitrile). INHIB was recovered in fraction 40, corresponding to the indicated peak (FIG. 19B).

Figure 20:
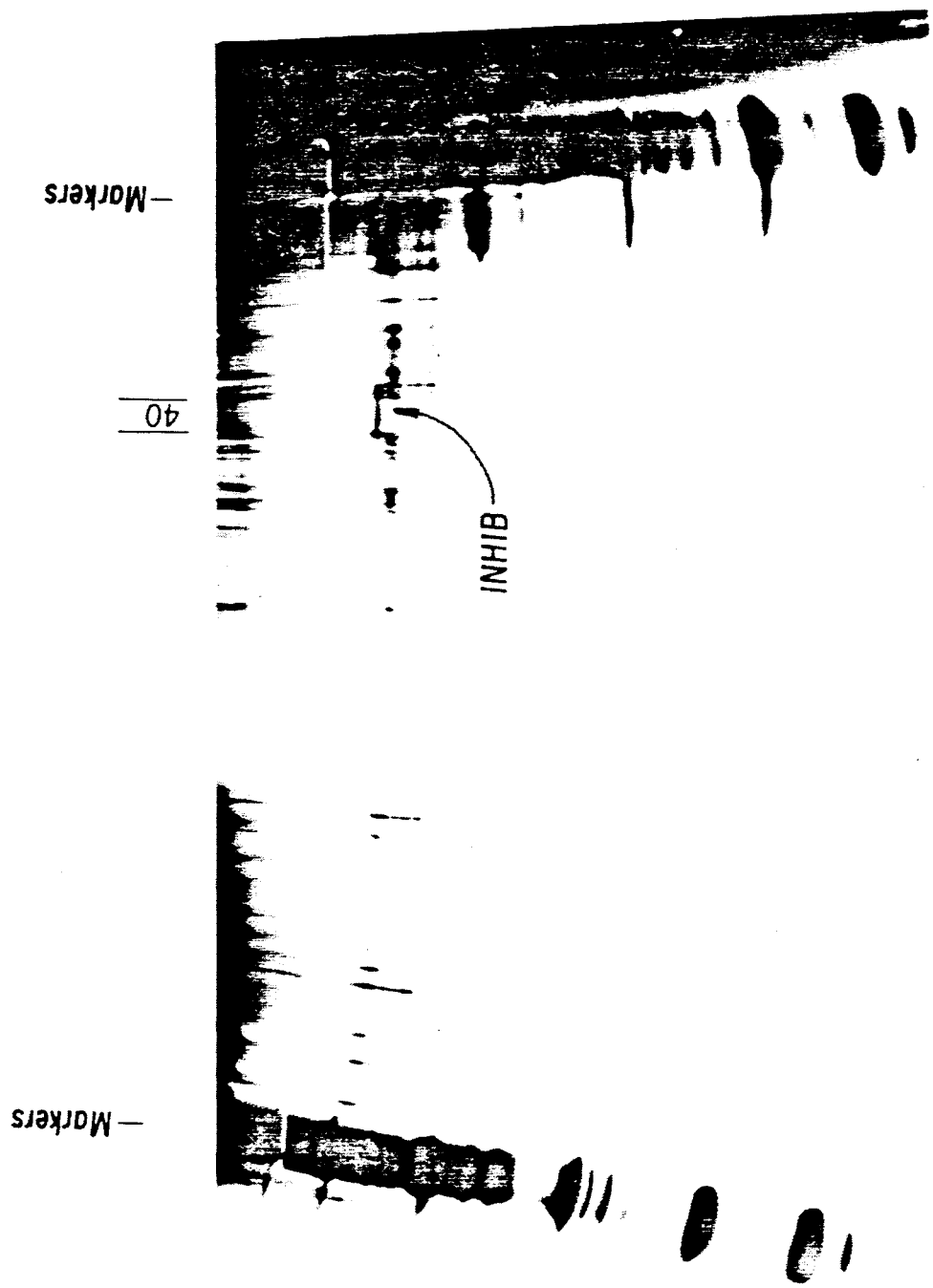
FIG. 20. SDS-polyacrylamide gel analysis of purified INHIB. The fraction numbers, corresponding to FIG. 19B and the positions of molecular weight markers, are shown. The single species of purified INHIB is indicated by an arrow.
Figure 21:
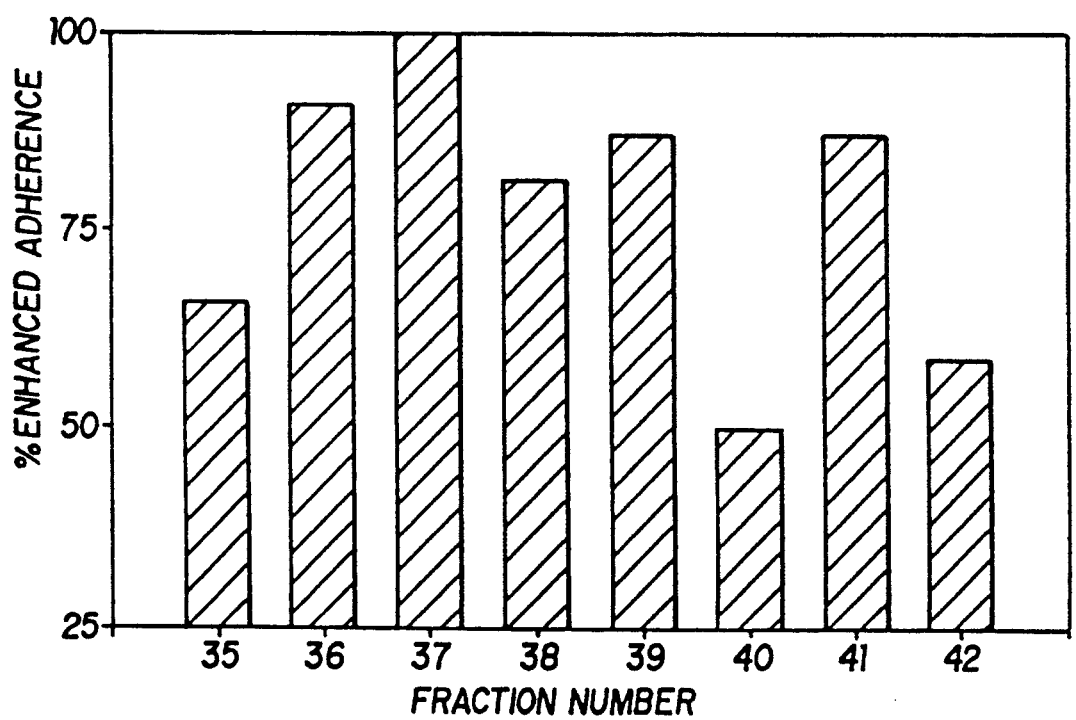
FIG. 21. The ability of purified INHIB to inhibit neutrophil adherence to plastic. The samples from FIGS. 19A and 19B were tested in two experiments as described in the text. The range of 0–100% is equal to the difference between the negative control and maximum adherence, assayed in duplicate in each of two experiments.

Analysis of this material by SDS-polyacrylamide gel showed a single polypeptide species with a molecular weight of approximately 70,000 (FIG. 20).

Affi-Gel Blue (Bio-Rad) fractionation of ammonium sulfate-precipitated human serum was also utilized in place of step (2), chromatography over controlled-pore glass beads. This step also greatly enhanced INHIB activity in the serum albumin-reduced fraction (greater than 100%) as assessed by the eosinophil cytoxicity assay and neutrophil adherence assay. There was some remaining activity in the albumin fraction which was not removed. (See Travis et al., *Biochem. J.* 157:301–306 (1976); Yip et al., *PNAS* 78:1601).

Mechanism of Action of INHIB

INHIB did not have detectable toxic effects on eosinophils. The presence of INHIB did not affect the uptake of trypan blue by eosinophils incubated in assay medium for periods up to 36 hours (not shown). Similarly, the presence of INHIB did not affect the uptake of trypan blue by non-adherent eosinophils removed from cytotoxicity cultures. Furthermore, eosinophils incubated in medium with INHIB for 1 or 12 hours synthesized $H_2O_2$ at the same rate a control incubated eosinophils, following stimulus with an optimal dose of phorbol myristate acetate (PMA).

In one experiment, for example, PMA increased the rate of $H_2O_2$ production by a factor 63.5 and 66.3 for eosinophils incubated 12 hours with and without an optimal dose of INHIB, while the increase was by a factor of only 30.3 after a 5 minute preincubation with 0.01% sodium azide.

Effect Of Cytokine

The inventors also investigated the question of the effects of INHIB as specific for TNF stimulation of eosinophils or whether INHIB would also suppress the function of GM-CSF-stimulated eosinophils. Selected control sera (#s 51, 52, 53, and 54 from the Red Cross collection, see Table 2) and various control HPLC sizing fractions (not shown) had no effect on the cytotoxic function of GM-CSF-stimulated eosinophils. On the other hand, NR serum, chromatographically-purified INHIB from NR serum, and selected samples with detectable INHIB (#s 25, 33, 41, and 67) all reduced by the cytotoxic function of GM-CSF-stimulated eosinophils (Table 2).

TABLE TWO

Effect of INHIB on the Cytotoxic Function of TNF and GM-CSF-stimulated Eosinophils

| | Cytokine Stimulation of Eosinophils | | |
|---|---|---|---|
| | None | 100 U/ml TNF | 20 pM GM-CSF |
| Inhibitor | | | |
| None | 9(a) | 48 | 100 |
| 10% NR serum | 23 | 24 | 33 |
| 20% INHIB(b) | 13 | 27 | 46 |
| Red Cross serum #(c): | | | |
| 51 | 7 | 37 | 92 |
| 52 | 11 | 46 | 70 |
| 53 | 6 | 51 | 89 |
| 54 | 12 | 35 | 83 |
| 25 | 7 | 7 | 22 |
| 33 | 10 | 11 | 25 |
| 41 | 12 | 17 | 25 |
| 67 | 15 | 12 | 36 |

(a)the % maximum killing of schistosomula assayed at 36 to 40 hours, mean of duplicate cultures.
(b)derived from NR serum, dilution factor relative to the serum = 50.
(c)samples 51 through 54 were selected for the absence of an inhibitory activity; 25, 33, 41 and 67 were selected for the presence of inhibitory activity (see FIG. 7).

Figure 11:
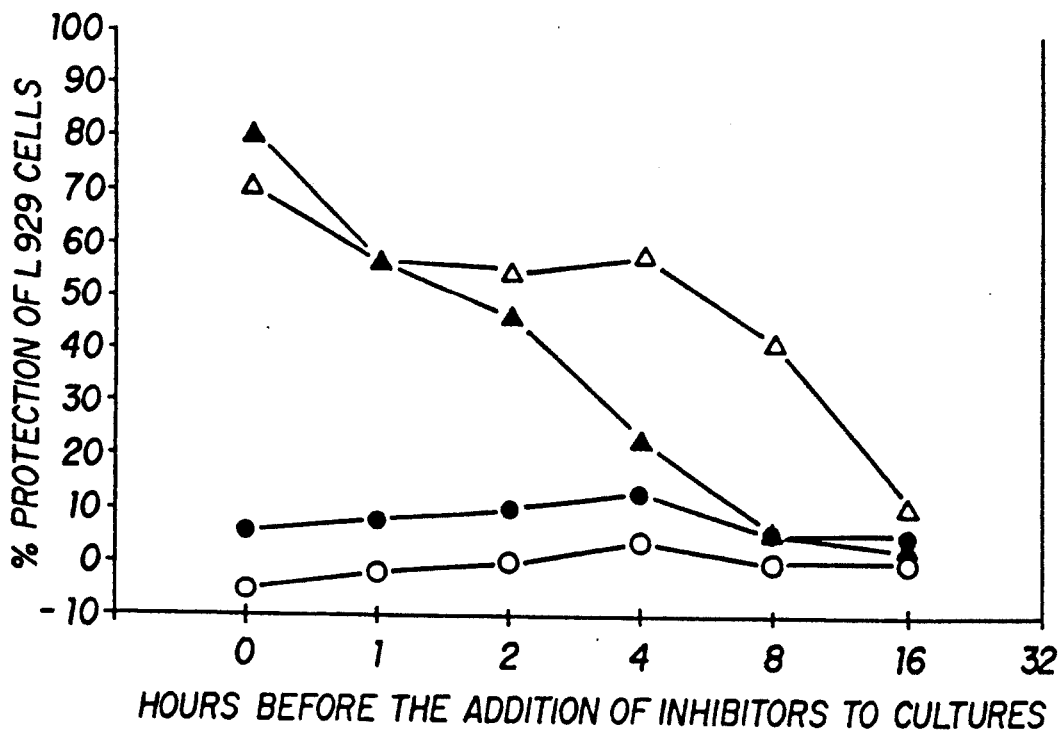
FIG. 11. The inability of INHIB to protect L929 cells from TNF; time dependence of protection by the neutralizing monoclonal antibody 245-10E11. 100 U/ml of TNF was added to actinomycin D-treated (solid symbols) or untreated (open symbols) L929 cells. At the indicated times, 20% INHIB (circles, HPLC fractions 7 through 9) or 1000 neutralizing units of monoclonal antibody (triangles) was added to the cultures. The survival of cells was measured by the MTT method, and the relative protection by either of the inhibitors was calculated by comparison with the no inhibitor (0%) and no TNF (100%) control values.
Figure 12:
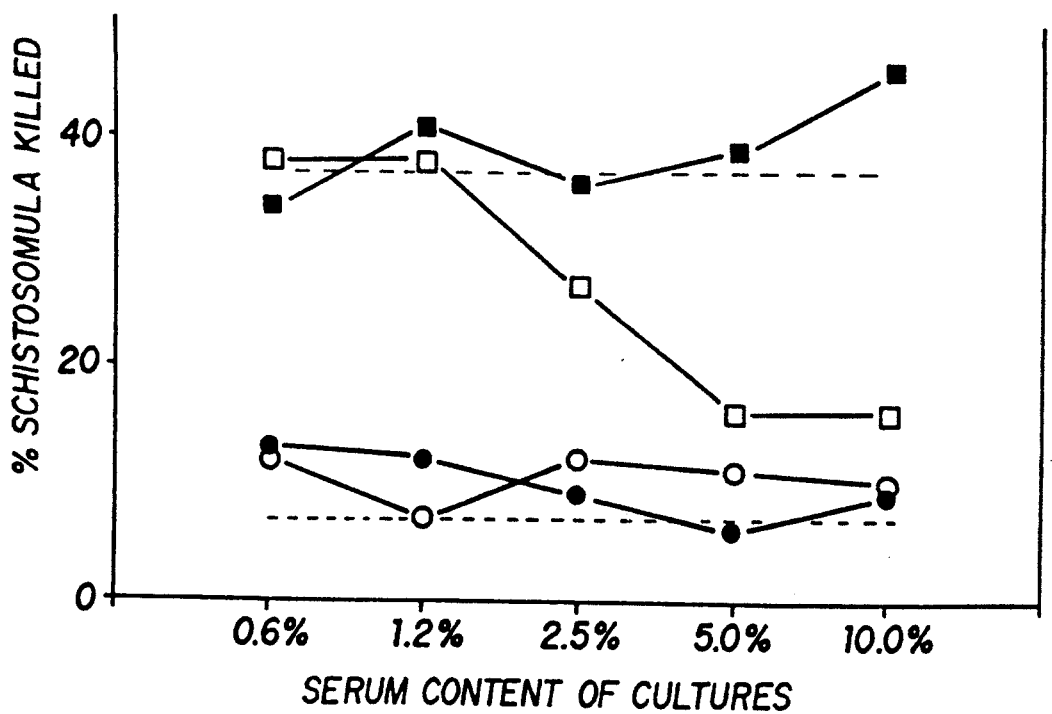
FIG. 12. The existence of a serum factor (INHIB) that inhibits the cytotoxic function of TNF-stimulated human eosinophils. Normal human serum (solid symbols) and serum from a subject with frequent episodes of allergic dermatitis (open symbols) were added to the eosinophil cytotoxicity assay (components=10$^5$ purified human eosinophils, antibody from Brazilian schistosomiasis patients, control medium [circles] or medium plus 100 U/ml of TNF [squares], and 100 mechanically transformed schistosomula) at the indicated concentrations. After a 40-hour incubation at 37° C., the killing of schistosomula targets was scored by microscopy. Values represent the mean od duplicate determinations.
Figure 13:
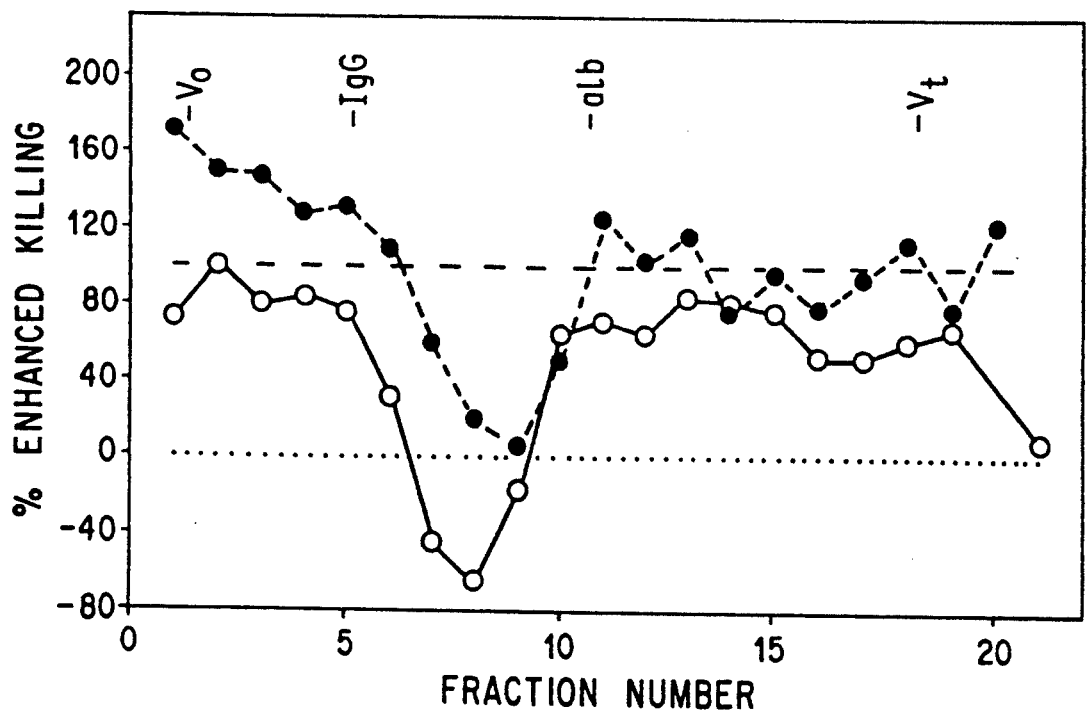
FIG. 13. Molecular weight estimate of the INHIB in normal (solid circle) and allergic dermatitis (open circle) sera. 100 ul samples of serum were chromatographed on a TSK-400 HPLC column with a solvent of Hank's Balanced Salt Solution (buffered with 25 mM Hepes, pH 7.0, and containing penicillin and streptomycin). The eluted samples were tested in the eosinophil cytotoxicity assay, as described in FIG. 12.
Figure 14:
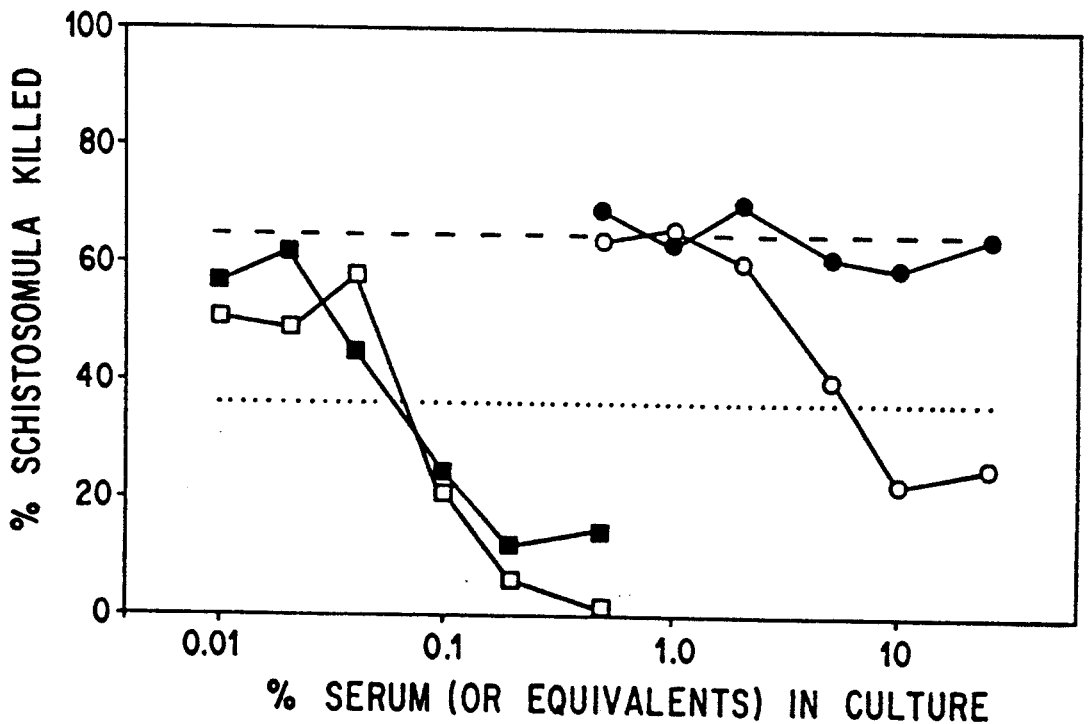
FIG. 14. Increased potency of INHIB as a result of partial purification. Pooled fractions 17-19 from FIG. 13 (squares) were compared for inhibitory activity to the sera (circles) from which they were derived. Samples from a normal (solid symbols) and allergic dermatitis subjects (open symbols) were tested at the indicated concentration in the eosinophil cytotoxicity assay, as described for FIG. 12.

INHIB did not protect L929 cells from the toxic effects of TNF either in the presence or absence of actinomycin D, when added to the culture after various times of incubation. In contrast, the TNF-specific monoclonal antibody 245-10E11, protected the L929 cells when added early in the culture period (FIG. 11).

The inhibitory effect of NR serum or INHIB on the cytotoxic function of TNF-stimulated eosinophils could be observed when they were added to the eosinophils as late as 4 hours after the TNF. Monoclonal antibody 245-10E11 also inhibited TNF-enhanced cytotoxic function, but only when it was added simultaneously with the TNF to the eosinophils.

The effect of INHIB was observed when it was present for the first 2 hours of culture. When it was removed by washing after shorter durations of culture, the effects were diminished or undetectable. Preincubation of eosinophils with INHIB for up to 12 hours at 37° C. and removal of INHIB by washing did not reduce the subsequent cytotoxic function of TNF-stimulated eosinophils.

EXAMPLE NINE

Separation of INHIB From Human Serum

Serum from a human subject with severe allergic dermatitis was brought to 50% saturation with ammonium sulfate at 0° C. overnight and centrifuged at 12,000 x g. The supernatant portion was brought to 65% saturation, reincubated, and centrifuged as above. The resulting pellet was dissolved and dialyzed in 0.04M sodium phosphate buffer, pH 7.2, and then incubated with controlled pore glass beads (one gram of beads per 10 ml of serum, Electonucleonics, Inc., Fairfield, N.J.). The beads were washed with 20% and then 30% ethylene glycol in the same buffer. Material from the 30% wash was subjected to dialysis in water and concentrated by lyophilization and applied to a TSK-Phenyl 5PW 7.5×75 mm column (HPLC). Bound proteins were eluted with a 45 minute gradient of 0.6M ammonium sulfate in 100 mM phosphate, pH 7.0., to 30% ethylene glycol in 10 mM phosphate, pH 7.0. The material collected from 28 to 31 minutes of the gradient was dialyzed in 0.02M TRIS, pH 7.0, and applied to a TSK-DEAE 5PW 7.5×75 mm column. Bound material was eluted with a 45 minute gradient to 0.5 M ammonium sulfate in the same buffer. The material collected from 10 to 13 minutes of this gradient was collected and applied to a Vydac C-4 4.6×250 mm column, washed with 0.1% trifluoroacetic acid, and eluted with a 60 minute gradient to 50% acetonitrile in 0.1% trifluoroacetic acid. The active material was recovered for 19 or 20 minutes of this gradient.

EXAMPLE TEN

Identification of INHIB as a 75 kDa Protein

Purified INHIB was analyzed for molecular weight by SDS polyacrylamide gel electrophoresis (according to Laemmli, Nature [London] 227: 680–685 (1970). After staining purified INHIB and molecular weight protein standards by electrophoresis, the proteins were stained with ammonical silver (Oakley et al., Anal. Biochem. 105:361–363 (1980)). Molecular weight was determined by interpolation on a semi-logarithmic scale of relative INHIB electrophoretic mobility in comparison to standards. INHIB was calculated to have a molecular weight of about 75 kDa.

EXAMPLE ELEVEN

Sequencing of INHIB

The 75 kDa polypeptide species identified in Example Ten was isolated following chromatography on a TSK-400 7×600 mm column (solvent=0.9% NaCl, 25 mM HEPES, pH 7.2, 100 U/ml penicillin G, and 100 ug/ml of streptomycin). The fraction containing INHIB (identified by eosinophil cytotoxicity assay) was separated by SDS-PAGE (10% polyacrylamide under reducing conditions). Polypeptide species were then transferred to PVDF membrane and stained with Coomassie blue. Material from an SDS-gel run in parallel was recovered by electroelution of gel slices. These samples were dialyzed in medium and tested for the ability to inhibit eosinophil cytotoxic function. The region of PVDF membrane containing the polypeptide species that was associated with inhibitory activity was then excised and submitted for amino acid sequence analysis. The analysis was performed using an Applied Biosystems Model 475A Gas Phase Protein Sequencer.

EXAMPLE TWELVE

Structural Comparison of INHIB With the Free β Chain

A computer search was carried out for the GenBank data base (version 61). A partial N terminal amino acid sequence for purified INHIB is shown in TABLE THREE and designated SEQ ID NO: 1. The computer search of known polypeptide sequences revealed strong homology of INHIB to the β (Seq. ID No. 2) chain of the C3 complement component (sequence aligned in TABLE THREE).

TABLE THREE

Purified INHIB (Seq. ID No. 1): Xaa—Pro—Met—Tyr—Ser—
C3 β-chain (Seq. ID No. 2): Ser—Pro—Met—Tyr—Ser—
Ile—Xaa—Thr—Pro—Asn—Xaa—Xaa—Xaa—Leu—Glu—Ser—Xaa—Glu—
Ile—Ile—Thr—Pro—Asn—Ile—Leu—Ala—Leu—Glu—Ser—Glu—Glu—
Xaa—Met . . .

TABLE THREE-continued

Thr—Met . . .

EXAMPLE THIRTEEN

Preparation of Free β Chain From Intact C3

Purified C3 (Hammer et al., *J. Biol. Chem.* 256:2995 (1981)) was reduced in 10% 2-mercaptoethanol for 1 hour at room temperature. In order to alkylate sulfhydryl groups, reduced material was mixed with an equal volume of 0.75M iodoacetamide on ice for 1 hour. Free β chain was isolated by preparative SDS-PAGE under reducing conditions and electroelution in 0.05M ammonium bicarbonate. Eluted protein and similarly processed material from other regions of the gels (control samples) were dialyzed in medium. Protein concentrations were determined by the Bradford method (Bradford, *Anal. Biochem.* 72:248-254 (1976).

EXAMPLE FOURTEEN

Eosinophil Cytotoxicity and Neutrophil Adherence of Intact C3 and Free β Chain C3

Human eosinophils, isolated at 80 to 99% purity (Vadas et al., *J. Immunol.* 122:1228 (1979)) were tested for the ability to kill larvae of *Schistosoma mansoni* in the presence of antibody and a test or control source of inhibitor. The eosinophils were treated with either 100 U/ml of purified recombinant tumor necrosis factor or (Cetus Corporation) or 20 pM purified recombinant granulocyte-macrophage colony-stimulating factor (Dr. Judith C. Gasson) in order to activate the killing functions, as described (Silberstein et al., *Proc. Natl. Acad. Sci. USA* 83:1055 (1986) and Silberstein et al., *J. Immunol.* 137:3290 (1986)).

Neutrophils were isolated at >95% purity by dextran sedimentation, centrifugation through a cushion of Ficoll-Hypaque (Pharmacia, Piscataway, N.J.), and hypotonic lysis to remove remaining erythrocytes. For assay of adherence to tissue culture plastic, $10^5$ neutrophils to tissue culture plate microwells (Falcon Labware, Oxnard, Calif.) in 200 µl of RPMI 1640 medium, containing 100 U/ml of penicillin G, 100 µg/ml of streptomycin, 8% NuSerum (Collaborative Research, Inc., Waltham, Mass.), and 2% heat-inactivated fetal calf serum (GIBCO, Grand Island, N.Y.). For certain test conditions media containing 100 U/ml recombinant tumor necrosis factor as well as a test or control source of inhibitor were used. The neutrophils were allowed to adhere at 37° C. for 2 hours, and then nonadherent cells were washed away with warm saline. The wells were emptied of liquid, and then filled with 200 µl of a solution containing 0.1% Triton X-100, 0.4 mM 2-2' azino-di-3-ethylbenzthiazoline-6-sulfonate plus 0.003% hydrogen peroxide in 0.05M sodium citrate, pH 4.0. The generation of colored product (absorbance monitored at 405 nm) reflected the quantity of cell-derived myeloperoxidase in the wells and correlated with visual assessments of cell adherence.

Intact C3 and the free β chain of Example 13 were assayed for activity with respect to eosinophil cytotoxicity and neutrophil adherence functions. Intact C3 had no inhibitory activity at concentrations as high as 300 µg/ml of protein. Reduction of C3, and particularly reduction and alkylation, to generate free β chain resulted in substantial inhibitory activity. Free β chain exhibited the greatest activity (half maximal at 250 ng/ml), though a mock preparation from an adjacent SDS-PAGE gel slice had no activity. Alkylation had no effect on the activity of free β chain, demonstrating the absence of a functional role for the reduced sulfhydryl groups.

EXAMPLE FIFTEEN

Assay of C3c Function

C3c is the C3 β chain attached to 41 and 25 kDa fragments of the α chain by disulfide bonds. C3c is generally considered the terminal cleavage product of C3 activation (Ross et al., *Adv. Immunol.* 37:217 (1985); Müller-Eberhard, In *Inflammation*, Gallin et al., editors, Raven Press, N.Y. (1985)). C3c was prepared by trypsin digestion of C3 according to the method of Bokisch (Bokisch et al., *J. Exp. Med* 129:1009 (1969) and tested in assays of eosinophil cytotoxic function and neutrophil adherence. Neither assay exhibited detectable inhibitory activity.

EXAMPLE SIXTEEN

Detection of INHIB With β Chain-Specific Monoclonal Antibodies

BALB/c mice were immunized with approximately 100 µg of purified C3 β chain in complete and subsequently incomplete Freund's adjuvant. Spleen cells were fused with SP2 myeloma cells and cultured in selective medium according to standard methods (Kohler et al., *Nature* 256:495-497 (1975); Davidson et al. *Somat. Cell Genet.* 2:165-176 (1976)). Hybridoma culture supernatants were screened by ELISA and Western Blot analysis for reactivity with free C3 β chain in reduced preparations of purified C3. Positive hybridoma lines were subcloned twice. Pooled culture supernatants of four positive hybridomas were used to screen for the presence of free C3 β chain in biological fluids by Western Blot analysis. One µl samples of biological fluids were separated by SDS-PAGE, and the resolved species were transferred electrophoretically to PVDF membrane (Burnette, *Anal. Biochem.* 112:195 (1981).

Free β chain was detected in plasma drawn from a human subject during a severe allergic dermatitis reaction and in synovial fluid of two patients with juvenile rheumatoid arthritis. No free β chain was detected in normal plasma or in blister fluid collected from the allergic dermatitis lesion. The presence of free β chain correlated with the ability of these biological fluids to inhibit eosinophil cytotoxic function.

While the invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of diagnosing the presence and location of inflammation in a mammalian subject suspected of having an inflammation which comprises:
   (a) administering to said subject a composition containing a detectably labeled binding molecule capable of identifying INHIB, wherein said INHIB comprises the amino acid sequence of SEQ ID NO:3; and
   (b) detecting said binding molecule.

2. A method of diagnosing the presence and location of an inflammation in a mammalian subject suspected of having an inflammation which comprises:
   (a) incubating a biological sample of said subject in the presence of a detectably labeled binding molecule capable of identifying INHIB wherein said INHIB comprises the amino acid sequence of SEQ ID NO:3; and
   (b) detecting said binding molecule which is bound in said sample.

3. A method of inhibiting inflammation in a mammalian subject which comprises providing to said subject in need of such treatment a pharmaceutical composition comprising INHIB in an inflammation reducing amount, wherein said INHIB comprises the amino acid sequence of SEQ ID NO:3.

4. The method of claim 3, wherein said inflammation is a reaction of the specific defense system.

5. The method of claim 3, wherein said inflammation is a reaction of the non-specific defense system.

6. The method of claim 3, wherein said inflammation is a delayed type hypersensitivity reaction.

7. The method of claim 3, wherein said inflammation is a symptom of an autoimmune disease.

8. The method of claim 7, wherein said autoimmune disease is selected from the group consisting of:
   (a) Raynaud's syndrome;
   (b) autoimmune thyroiditis;
   (c) experimental allergic encephalomyelitis
   (d) multiple sclerosis;
   (e) rheumatoid arthritis; and
   (f) lupus erythematosus.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: both ( i i ) MOLECULE TYPE: peptide ( x i ) SEQUENCE DESCRIPTION: SEQ ID NO:1:

```
Xaa  Pro  Met  Tyr  Ser  Ile  Xaa  Thr  Pro  Asn  Xaa  Xaa  Xaa  Leu  Glu  Ser
 1              5                        10                       15
Xaa  Glu  Xaa  Met
           20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( D ) TOPOLOGY: both ( i i ) MOLECULE TYPE: peptide ( x i ) SEQUENCE DESCRIPTION: SEQ ID NO:2:

```
Ser  Pro  Met  Tyr  Ser  Ile  Ile  Thr  Pro  Asn  Ile  Leu  Ala  Leu  Glu  Ser
 1              5                        10                       15
Glu  Glu  Thr  Met
           20
```

( 2 ) INFORMATION FOR SEQ ID NO:3:

( i ) SEQUENCE CHARACTERISTICS:
        ( A ) LENGTH: 645 amino acids
        ( B ) TYPE: amino acid
        ( D ) TOPOLOGY: both ( i i ) MOLECULE TYPE: peptide ( x i ) SEQUENCE DESCRIPTION: SEQ ID NO:3:

```
Ser  Pro  Met  Tyr  Ser  Ile  Ile  Thr  Pro  Asn  Ile  Leu  Arg  Leu  Glu  Ser
 1              5                        10                       15
Glu  Glu  Thr  Met  Val  Leu  Glu  Ala  His  Asp  Ala  Gln  Gly  Asp  Val  Pro
           20                       25                       30
Val  Thr  Val  Thr  Val  His  Asp  Phe  Pro  Gly  Lys  Lys  Leu  Val  Leu  Ser
           35                       40                       45
Ser  Glu  Lys  Thr  Val  Leu  Thr  Pro  Ala  Thr  Asn  His  Met  Gly  Asn  Val
     50                       55                       60
Thr  Phe  Thr  Ile  Pro  Ala  Asn  Arg  Glu  Phe  Lys  Ser  Glu  Lys  Gly  Arg
 65                       70                       75                       80
Asn  Lys  Phe  Val  Thr  Val  Gln  Ala  Thr  Phe  Asx  Thr  Gln  Val  Val  Glu
                     85                       90                       95
Lys  Val  Leu  Leu  Val  Ser  Leu  Gln  Ser  Gly  Tyr  Leu  Phe  Ile  Gln  Thr
               100                      105                      110
Asp  Lys  Thr  Ile  Tyr  Thr  Pro  Gly  Ser  Thr  Val  Leu  Tyr  Arg  Ile  Phe
               115                      120                      125
Thr  Val  Asn  His  Lys  Leu  Leu  Pro  Val  Asx  Arg  Thr  Val  Met  Val  Asn
           130                      135                      140
```

-continued

| | | | | | | | | | | | | | | | |
|---|---|---|---|---|---|---|---|---|---|---|---|---|---|---|---|
| Ile | Glu | Asn | Pro | Glu | Gly | Ile | Pro | Val | Lys | Gln | Asp | Ser | Leu | Ser | Ser |
| 145 | | | | 150 | | | | | 155 | | | | | | 160 |
| Gln | Asn | Gln | Leu | Gly | Val | Leu | Pro | Leu | Ser | Trp | Asp | Ile | Pro | Glu | Leu |
| | | | | 165 | | | | | 170 | | | | | 175 | |
| Val | Asn | Met | Gly | Gln | Trp | Lys | Ile | Arg | Ala | Tyr | Tyr | Glu | Asn | Ser | Pro |
| | | | 180 | | | | | 185 | | | | | 190 | | |
| Gln | Gln | Val | Phe | Ser | Thr | Glu | Phe | Glu | Val | Lys | Glu | Tyr | Val | Leu | Pro |
| | | | 195 | | | | | 200 | | | | | 205 | | |
| Ser | Phe | Glu | Val | Ile | Val | Glu | Pro | Thr | Glu | Lys | Phe | Tyr | Tyr | Ile | Tyr |
| | 210 | | | | | 215 | | | | | 220 | | | | |
| Asn | Glu | Lys | Gly | Leu | Glu | Val | Thr | Ile | Thr | Ala | Arg | Phe | Leu | Tyr | Gly |
| 225 | | | | | 230 | | | | 235 | | | | | | 240 |
| Lys | Lys | Val | Glu | Gly | Thr | Ala | Phe | Val | Ile | Phe | Gly | Ile | Gln | Asp | Gly |
| | | | | 245 | | | | | 250 | | | | | 255 | |
| Glu | Gln | Arg | Ile | Ser | Leu | Pro | Glu | Ser | Leu | Lys | Arg | Ile | Pro | Ile | Glu |
| | | | | 260 | | | | | 265 | | | | | 270 | |
| Asp | Gly | Ser | Gly | Glu | Val | Val | Leu | Ser | Arg | Lys | Val | Leu | Leu | Asp | Gly |
| | | | 275 | | | | | 280 | | | | | 285 | | |
| Val | Gln | Asn | Leu | Arg | Ala | Glu | Asp | Leu | Val | Gly | Lys | Ser | Leu | Tyr | Val |
| | 290 | | | | | 295 | | | | | 300 | | | | |
| Ser | Ala | Thr | Val | Ile | Leu | His | Ser | Gly | Ser | Asp | Met | Val | Gln | Ala | Glu |
| 305 | | | | | 310 | | | | 315 | | | | | | 320 |
| Arg | Ser | Gly | Ile | Pro | Ile | Val | Thr | Ser | Pro | Tyr | Gln | Ile | His | Phe | Thr |
| | | | | 325 | | | | | 330 | | | | | 335 | |
| Lys | Thr | Pro | Lys | Tyr | Phe | Lys | Pro | Gly | Met | Pro | Phe | Asp | Leu | Met | Val |
| | | | 340 | | | | | 345 | | | | | 350 | | |
| Phe | Val | Thr | Asn | Pro | Asp | Gly | Ser | Pro | Ala | Tyr | Arg | Val | Pro | Val | Ala |
| | | | 355 | | | | | 360 | | | | | 365 | | |
| Val | Gln | Gly | Glu | Asp | Thr | Val | Gln | Ser | Leu | Thr | Gln | Gly | Asp | Gly | Val |
| | | 370 | | | | | 375 | | | | | 380 | | | |
| Ala | Lys | Leu | Ser | Ile | Asn | Thr | His | Pro | Ser | Gln | Lys | Pro | Leu | Ser | Ile |
| 385 | | | | | 390 | | | | | 395 | | | | | 400 |
| Thr | Val | Arg | Thr | Lys | Lys | Gln | Glu | Leu | Ser | Glu | Ala | Glu | Gln | Ala | Thr |
| | | | | 405 | | | | | 410 | | | | | 415 | |
| Arg | Thr | Met | Gln | Ala | Leu | Pro | Tyr | Ser | Thr | Val | Gly | Asn | Ser | Asn | Asn |
| | | | 420 | | | | | 425 | | | | | 430 | | |
| Tyr | Leu | His | Leu | Ser | Val | Leu | Thr | Thr | Glu | Leu | Arg | Pro | Gly | Glu | Thr |
| | | 435 | | | | | 440 | | | | | 445 | | | |
| Leu | Asn | Val | Asn | Phe | Leu | Leu | Arg | Met | Asp | Arg | Ala | His | Glu | Ala | Lys |
| | 450 | | | | | 455 | | | | | 460 | | | | |
| Ile | Arg | Tyr | Tyr | Thr | Tyr | Leu | Ile | Met | Asn | Lys | Gly | Arg | Leu | Leu | Lys |
| 465 | | | | | 470 | | | | | 475 | | | | | 480 |
| Ala | Gly | Arg | Gln | Val | Arg | Glu | Pro | Gly | Gln | Asp | Leu | Val | Val | Leu | Pro |
| | | | | 485 | | | | | 490 | | | | | 495 | |
| Leu | Ser | Ile | Thr | Thr | Asp | Phe | Ile | Pro | Ser | Phe | Arg | Leu | Val | Ala | Tyr |
| | | | 500 | | | | | 505 | | | | | 510 | | |
| Tyr | Thr | Val | Ile | Gly | Ala | Ser | Gly | Gln | Arg | Glu | Val | Val | Ala | Asp | Ser |
| | | 515 | | | | | 520 | | | | | 525 | | | |
| Val | Trp | Val | Asp | Val | Lys | Asp | Ser | Cys | Val | Gly | Ser | Leu | Val | Val | Lys |
| | | 530 | | | | | 535 | | | | | 540 | | | |
| Ser | Gly | Gln | Ser | Glu | Asp | Arg | Gln | Pro | Val | Pro | Gly | Gln | Gln | Met | Thr |
| 545 | | | | | 550 | | | | | 555 | | | | | 560 |
| Leu | Lys | Ile | Glu | Gly | Asp | His | Gly | Ala | Arg | Val | Val | Leu | Val | Ala | Val |
| | | | | 565 | | | | | 570 | | | | | 575 | |
| Asp | Lys | Gly | Val | Phe | Val | Leu | Asn | Lys | Lys | Asn | Lys | Leu | Thr | Gln | Ser |

|  | 580 |  |  |  |  | 585 |  |  |  |  | 590 |  |  |  |
|---|---|---|---|---|---|---|---|---|---|---|---|---|---|---|
| Lys | Ile | Trp | Asp | Val | Val | Glu | Lys | Ala | Asp | Ile | Gly | Cys | Thr | Pro | Gly |
|  |  | 595 |  |  |  |  | 600 |  |  |  |  | 605 |  |  |  |
| Ser | Gly | Lys | Asp | Tyr | Ala | Gly | Val | Phe | Ser | Asp | Ala | Gly | Leu | Thr | Phe |
|  | 610 |  |  |  |  | 615 |  |  |  |  | 620 |  |  |  |  |
| Thr | Ser | Ser | Ser | Gly | Gln | Gln | Thr | Ala | Gln | Arg | Ala | Glu | Leu | Gln | Cys |
| 625 |  |  |  |  | 630 |  |  |  |  | 635 |  |  |  |  | 640 |
| Pro | Gln | Pro | Ala | Ala |
|  |  |  |  | 645 |